(12) United States Patent
Ochs et al.

(10) Patent No.: US 8,337,846 B2
(45) Date of Patent: Dec. 25, 2012

(54) IMMUNOGENIC POLYPEPTIDES AND MONOCLONAL ANTIBODIES

(75) Inventors: Martina Ochs, Toronto (CA); Roger Brookes, Toronto (CA); Robert Charlebois, Toronto (CA); Jeremy Yethon, Milton (CA)

(73) Assignee: Sanofi Pasteur Limited, Toronto, Ontario (CA)

( * ) Notice: Subject to any disclaimer, the term of this patent is extended or adjusted under 35 U.S.C. 154(b) by 0 days.

(21) Appl. No.: 12/670,150

(22) PCT Filed: Jul. 23, 2008

(86) PCT No.: PCT/CA2008/001353
§ 371 (c)(1),
(2), (4) Date: Jun. 21, 2010

(87) PCT Pub. No.: WO2009/012588
PCT Pub. Date: Jan. 29, 2009

(65) Prior Publication Data
US 2010/0297133 A1    Nov. 25, 2010

Related U.S. Application Data

(60) Provisional application No. 60/961,723, filed on Jul. 23, 2007.

(51) Int. Cl.
*A61K 39/395* (2006.01)
*C07K 16/12* (2006.01)
(52) U.S. Cl. ............... 424/139.1; 424/150.1; 530/387.9; 530/388.4; 530/391.3
(58) Field of Classification Search .................... None
See application file for complete search history.

(56) References Cited

U.S. PATENT DOCUMENTS

| | | | |
|---|---|---|---|
| 5,837,541 A * | 11/1998 | Raff .............................. 435/340 |
| 6,582,706 B1 | 6/2003 | Johnson et al. |
| 7,074,415 B2 * | 7/2006 | Hamel et al. ................ 424/244.1 |
| 7,122,194 B2 | 10/2006 | Johnson et al. |
| 7,128,918 B1 * | 10/2006 | Hamel et al. ................ 424/244.1 |
| 7,262,024 B2 * | 8/2007 | Hamel et al. ................. 435/69.1 |
| 7,635,482 B2 * | 12/2009 | Hamel et al. ................ 424/190.1 |
| 7,635,487 B2 * | 12/2009 | Meinke et al. ............... 424/244.1 |
| 2003/0021795 A1 * | 1/2003 | Houston et al. ............. 424/185.1 |
| 2003/0077293 A1 * | 4/2003 | Hamel et al. ................ 424/190.1 |
| 2003/0232976 A1 * | 12/2003 | Hamel et al. .................. 536/23.1 |
| 2004/0081662 A1 | 4/2004 | Hermand et al. |
| 2005/0214329 A1 | 9/2005 | Laferriere et al. |
| 2006/0177465 A1 * | 8/2006 | Hamel et al. ................ 424/190.1 |
| 2006/0263846 A1 * | 11/2006 | Meinke et al. ............... 435/69.1 |
| 2009/0214537 A1 * | 8/2009 | Soriani et al. ............... 424/135.1 |

FOREIGN PATENT DOCUMENTS

| WO | 93/09811 | * | 5/1993 |
| WO | 00/37105 | * | 6/2000 |
| WO | 0039299 A2 | * | 7/2000 |
| WO | 2004/092209 | * | 10/2004 |

OTHER PUBLICATIONS

Tai, Stanley S, Critical Reviews in Microbiology, vol. 32, pp. 139-153, 2006, *Streptococcus pneumoniae* Protein Vaccine Candidates Properties, Activities and Animal Studies.*
Holmlund, E et al, Clinical VAccine Immunology, vol. 10, pp. 1-33, Apr. 29, 2009, Antibodies to Pneumococcal Proteins PhtD, CbpA and LytC in Filipino Pregant Women and Their infants in Relation to Pneumococcal Carriage.*
Adamou, et al. Identification and Characterization of a Novel Family of Pneumococcal Proteins That Are Protective against Sepsis. Infect Immun. 69:949-958 (2001).
Hamel, et al. Prevention of Pneumococcal Disease in Mice Immunized with Conserved Surface-Accessible Proteins. Infect Immun. 72:2659-26 (2004).
Ogunniyi, et al. Development of a vaccine against invasive pneumococcal disease based on combinations of virulence proteins of *Streptococcus pneumoniae*. Infect Immun. 75:350-35 (2007).
Zhang, et al. Recombinant PhpA protein, a unique histidine motif-containing protein from *Streptococcus pneumoniae*, protects mice against intranasal pneumococcal disease. Infect Immun. 69: 3827-3836 (2007).
Gulimi, et al. New approaches towards the identification antibiotic and vaccine targets in *Streptococcus pneumoniae*. EMBO reports 3, 8, 728-734 (2002).
Barocchi, et al. Vaccines in the era of genomics: The pneumococcal challenge. Vaccine, 25(16): 2963-2973 (2007).

* cited by examiner

Primary Examiner — Albert Navarro
Assistant Examiner — Ginny Portner
(74) Attorney, Agent, or Firm — Patrick J. Halloran; Reza Yacoob

(57) ABSTRACT

Provided herein are compositions and methods for eliciting an immune response against *Streptococcus pneumoniae*. More particularly, the compositions and methods relate to immunogenic polypeptides, including fragments of PhtD and variants thereof, and nucleic acids, vectors and transfected cells that encode or express the polypeptides. Methods of making and using the immunogenic polypeptides are also described.

10 Claims, No Drawings

SEQUENCE LISTING

<160> NUMBER OF SEQ ID NOS: 26

<210> SEQ ID NO 1
<211> LENGTH: 839
<212> TYPE: PRT
<213> ORGANISM: Streptococcus pneumoniae

<400> SEQUENCE: 1

```
Met Lys Ile Asn Lys Lys Tyr Leu Ala Gly Ser Val Ala Val Leu Ala
1               5                   10                  15

Leu Ser Val Cys Ser Tyr Glu Leu Gly Arg His Gln Ala Gly Gln Val
            20                  25                  30

Lys Lys Glu Ser Asn Arg Val Ser Tyr Ile Asp Gly Asp Gln Ala Gly
        35                  40                  45

Gln Lys Ala Glu Asn Leu Thr Pro Asp Glu Val Ser Lys Arg Glu Gly
    50                  55                  60

Ile Asn Ala Glu Gln Ile Val Lys Ile Thr Asp Gln Gly Tyr Val
65                  70                  75                  80

Thr Ser His Gly Asp His Tyr His Tyr Tyr Asn Gly Lys Val Pro Tyr
                85                  90                  95

Asp Ala Ile Ile Ser Glu Glu Leu Leu Met Lys Asp Pro Asn Tyr Gln
            100                 105                 110

Leu Lys Asp Ser Asp Ile Val Asn Glu Ile Lys Gly Gly Tyr Val Ile
        115                 120                 125

Lys Val Asp Gly Lys Tyr Tyr Val Tyr Leu Lys Asp Ala Ala His Ala
    130                 135                 140

Asp Asn Ile Arg Thr Lys Glu Glu Ile Lys Arg Gln Lys Gln Glu His
145                 150                 155                 160

Ser His Asn His Gly Gly Gly Ser Asn Asp Gln Ala Val Val Ala Ala
                165                 170                 175

Arg Ala Gln Gly Arg Tyr Thr Thr Asp Asp Gly Tyr Ile Phe Asn Ala
            180                 185                 190

Ser Asp Ile Ile Glu Asp Thr Gly Asp Ala Tyr Ile Val Pro His Gly
        195                 200                 205

Asp His Tyr His Tyr Ile Pro Lys Asn Glu Leu Ser Ala Ser Glu Leu
    210                 215                 220

Ala Ala Ala Glu Ala Tyr Trp Asn Gly Lys Gln Gly Ser Arg Pro Ser
225                 230                 235                 240

Ser Ser Ser Ser Tyr Asn Ala Asn Pro Ala Gln Pro Arg Leu Ser Glu
                245                 250                 255

Asn His Asn Leu Thr Val Thr Pro Thr Tyr His Gln Asn Gln Gly Glu
            260                 265                 270

Asn Ile Ser Ser Leu Leu Arg Glu Leu Tyr Ala Lys Pro Leu Ser Glu
        275                 280                 285

Arg His Val Glu Ser Asp Gly Leu Ile Phe Asp Pro Ala Gln Ile Thr
    290                 295                 300

Ser Arg Thr Ala Arg Gly Val Ala Val Pro His Gly Asn His Tyr His
305                 310                 315                 320

Phe Ile Pro Tyr Glu Gln Met Ser Glu Leu Glu Lys Arg Ile Ala Arg
                325                 330                 335

Ile Ile Pro Leu Arg Tyr Arg Ser Asn His Trp Val Pro Asp Ser Arg
            340                 345                 350

Pro Glu Gln Pro Ser Pro Gln Ser Thr Pro Glu Pro Ser Pro Ser Pro
        355                 360                 365
```

```
Gln Pro Ala Pro Asn Pro Gln Pro Ala Pro Ser Asn Pro Ile Asp Glu
    370                 375                 380

Lys Leu Val Lys Glu Ala Val Arg Lys Val Gly Asp Gly Tyr Val Phe
385                 390                 395                 400

Glu Glu Asn Gly Val Ser Arg Tyr Ile Pro Ala Lys Asp Leu Ser Ala
                405                 410                 415

Glu Thr Ala Ala Gly Ile Asp Ser Lys Leu Ala Lys Gln Glu Ser Leu
            420                 425                 430

Ser His Lys Leu Gly Ala Lys Lys Thr Asp Leu Pro Ser Ser Asp Arg
        435                 440                 445

Glu Phe Tyr Asn Lys Ala Tyr Asp Leu Leu Ala Arg Ile His Gln Asp
    450                 455                 460

Leu Leu Asp Asn Lys Gly Arg Gln Val Asp Phe Glu Ala Leu Asp Asn
465                 470                 475                 480

Leu Leu Glu Arg Leu Lys Asp Val Pro Ser Asp Lys Val Lys Leu Val
                485                 490                 495

Asp Asp Ile Leu Ala Phe Leu Ala Pro Ile Arg His Pro Glu Arg Leu
            500                 505                 510

Gly Lys Pro Asn Ala Gln Ile Thr Tyr Thr Asp Asp Glu Ile Gln Val
        515                 520                 525

Ala Lys Leu Ala Gly Lys Tyr Thr Thr Glu Asp Gly Tyr Ile Phe Asp
    530                 535                 540

Pro Arg Asp Ile Thr Ser Asp Glu Gly Asp Ala Tyr Val Thr Pro His
545                 550                 555                 560

Met Thr His Ser His Trp Ile Lys Lys Asp Ser Leu Ser Glu Ala Glu
                565                 570                 575

Arg Ala Ala Ala Gln Ala Tyr Ala Lys Glu Lys Gly Leu Thr Pro Pro
            580                 585                 590

Ser Thr Asp His Gln Asp Ser Gly Asn Thr Glu Ala Lys Gly Ala Glu
        595                 600                 605

Ala Ile Tyr Asn Arg Val Lys Ala Ala Lys Lys Val Pro Leu Asp Arg
    610                 615                 620

Met Pro Tyr Asn Leu Gln Tyr Thr Val Glu Val Lys Asn Gly Ser Leu
625                 630                 635                 640

Ile Ile Pro His Tyr Asp His Tyr His Asn Ile Lys Phe Glu Trp Phe
                645                 650                 655

Asp Glu Gly Leu Tyr Glu Ala Pro Lys Gly Tyr Thr Leu Glu Asp Leu
            660                 665                 670

Leu Ala Thr Val Lys Tyr Tyr Val Glu His Pro Asn Glu Arg Pro His
        675                 680                 685

Ser Asp Asn Gly Phe Gly Asn Ala Ser Asp His Val Arg Lys Asn Lys
    690                 695                 700

Val Asp Gln Asp Ser Lys Pro Asp Glu Asp Lys Glu His Asp Glu Val
705                 710                 715                 720

Ser Glu Pro Thr His Pro Glu Ser Asp Glu Lys Glu Asn His Ala Gly
                725                 730                 735

Leu Asn Pro Ser Ala Asp Asn Leu Tyr Lys Pro Ser Thr Asp Thr Glu
            740                 745                 750

Glu Thr Glu Glu Glu Ala Glu Asp Thr Thr Asp Glu Ala Glu Ile Pro
        755                 760                 765

Gln Val Glu Asn Ser Val Ile Asn Ala Lys Ile Ala Asp Ala Glu Ala
    770                 775                 780

Leu Leu Glu Lys Val Thr Asp Pro Ser Ile Arg Gln Asn Ala Met Glu
```

```
                785                 790                 795                 800
Thr Leu Thr Gly Leu Lys Ser Ser Leu Leu Gly Thr Lys Asp Asn
                805                 810                 815
Asn Thr Ile Ser Ala Glu Val Asp Ser Leu Ala Leu Leu Lys Glu
                820                 825                 830
Ser Gln Pro Ala Pro Ile Gln
                835

<210> SEQ ID NO 2
<211> LENGTH: 493
<212> TYPE: PRT
<213> ORGANISM: Streptococcus pneumoniae

<400> SEQUENCE: 2

Trp Val Pro Asp Ser Arg Pro Glu Gln Pro Ser Pro Gln Ser Thr Pro
1               5                   10                  15
Glu Pro Ser Pro Ser Pro Gln Pro Ala Pro Asn Pro Gln Pro Ala Pro
                20                  25                  30
Ser Asn Pro Ile Asp Glu Lys Leu Val Lys Glu Ala Val Arg Lys Val
                35                  40                  45
Gly Asp Gly Tyr Val Phe Glu Glu Asn Gly Val Ser Arg Tyr Ile Pro
        50                  55                  60
Ala Lys Asp Leu Ser Ala Glu Thr Ala Ala Gly Ile Asp Ser Lys Leu
65              70                  75                  80
Ala Lys Gln Glu Ser Leu Ser His Lys Leu Gly Ala Lys Lys Thr Asp
                85                  90                  95
Leu Pro Ser Ser Asp Arg Glu Phe Tyr Asn Lys Ala Tyr Asp Leu Leu
                100                 105                 110
Ala Arg Ile His Gln Asp Leu Leu Asp Asn Lys Gly Arg Gln Val Asp
                115                 120                 125
Phe Glu Ala Leu Asp Asn Leu Leu Glu Arg Leu Lys Asp Val Pro Ser
        130                 135                 140
Asp Lys Val Lys Leu Val Asp Asp Ile Leu Ala Phe Leu Ala Pro Ile
145             150                 155                 160
Arg His Pro Glu Arg Leu Gly Lys Pro Asn Ala Gln Ile Thr Tyr Thr
                165                 170                 175
Asp Asp Glu Ile Gln Val Ala Lys Leu Ala Gly Lys Tyr Thr Thr Glu
                180                 185                 190
Asp Gly Tyr Ile Phe Asp Pro Arg Asp Ile Thr Ser Asp Glu Gly Asp
        195                 200                 205
Ala Tyr Val Thr Pro His Met Thr His Ser His Trp Ile Lys Lys Asp
210             215                 220
Ser Leu Ser Glu Ala Glu Arg Ala Ala Ala Gln Ala Tyr Ala Lys Glu
225             230                 235                 240
Lys Gly Leu Thr Pro Pro Ser Thr Asp His Gln Asp Ser Gly Asn Thr
                245                 250                 255
Glu Ala Lys Gly Ala Glu Ala Ile Tyr Asn Arg Val Lys Ala Ala Lys
                260                 265                 270
Lys Val Pro Leu Asp Arg Met Pro Tyr Asn Leu Gln Tyr Thr Val Glu
        275                 280                 285
Val Lys Asn Gly Ser Leu Ile Ile Pro His Tyr Asp His Tyr His Asn
                290                 295                 300
Ile Lys Phe Glu Trp Phe Asp Glu Gly Leu Tyr Glu Ala Pro Lys Gly
305             310                 315                 320
Tyr Thr Leu Glu Asp Leu Leu Ala Thr Val Lys Tyr Tyr Val Glu His
```

```
                         325                 330                 335
Pro Asn Glu Arg Pro His Ser Asp Asn Gly Phe Gly Asn Ala Ser Asp
                340                 345                 350

His Val Arg Lys Asn Lys Val Asp Gln Asp Ser Lys Pro Asp Glu Asp
            355                 360                 365

Lys Glu His Asp Glu Val Ser Glu Pro Thr His Pro Glu Ser Asp Glu
        370                 375                 380

Lys Glu Asn His Ala Gly Leu Asn Pro Ser Ala Asp Asn Leu Tyr Lys
385                 390                 395                 400

Pro Ser Thr Asp Thr Glu Glu Thr Glu Glu Glu Ala Glu Asp Thr Thr
                405                 410                 415

Asp Glu Ala Glu Ile Pro Gln Val Glu Asn Ser Val Ile Asn Ala Lys
                420                 425                 430

Ile Ala Asp Ala Glu Ala Leu Leu Glu Lys Val Thr Asp Pro Ser Ile
            435                 440                 445

Arg Gln Asn Ala Met Glu Thr Leu Thr Gly Leu Lys Ser Ser Leu Leu
        450                 455                 460

Leu Gly Thr Lys Asp Asn Asn Thr Ile Ser Ala Glu Val Asp Ser Leu
465                 470                 475                 480

Leu Ala Leu Leu Lys Glu Ser Gln Pro Ala Pro Ile Gln
                485                 490

<210> SEQ ID NO 3
<211> LENGTH: 164
<212> TYPE: PRT
<213> ORGANISM: Streptococcus pneumoniae

<400> SEQUENCE: 3

Val Lys Tyr Tyr Val Glu His Pro Asn Glu Arg Pro His Ser Asp Asn
1               5                   10                  15

Gly Phe Gly Asn Ala Ser Asp His Val Arg Lys Asn Lys Val Asp Gln
            20                  25                  30

Asp Ser Lys Pro Asp Glu Asp Lys Glu His Asp Glu Val Ser Glu Pro
        35                  40                  45

Thr His Pro Glu Ser Asp Glu Lys Glu Asn His Ala Gly Leu Asn Pro
    50                  55                  60

Ser Ala Asp Asn Leu Tyr Lys Pro Ser Thr Asp Thr Glu Glu Thr Glu
65                  70                  75                  80

Glu Glu Ala Glu Asp Thr Thr Asp Glu Ala Glu Ile Pro Gln Val Glu
                85                  90                  95

Asn Ser Val Ile Asn Ala Lys Ile Ala Asp Ala Glu Ala Leu Leu Glu
            100                 105                 110

Lys Val Thr Asp Pro Ser Ile Arg Gln Asn Ala Met Glu Thr Leu Thr
        115                 120                 125

Gly Leu Lys Ser Ser Leu Leu Leu Gly Thr Lys Asp Asn Asn Thr Ile
    130                 135                 140

Ser Ala Glu Val Asp Ser Leu Leu Ala Leu Leu Lys Glu Ser Gln Pro
145                 150                 155                 160

Ala Pro Ile Gln

<210> SEQ ID NO 4
<211> LENGTH: 141
<212> TYPE: PRT
<213> ORGANISM: Streptococcus pneumoniae

<400> SEQUENCE: 4
```

```
His Val Arg Lys Asn Lys Val Asp Gln Asp Ser Lys Pro Asp Glu Asp
1               5                   10                  15

Lys Glu His Asp Glu Val Ser Glu Pro Thr His Pro Glu Ser Asp Glu
            20                  25                  30

Lys Glu Asn His Ala Gly Leu Asn Pro Ser Ala Asp Asn Leu Tyr Lys
        35                  40                  45

Pro Ser Thr Asp Thr Glu Glu Thr Glu Glu Ala Glu Asp Thr Thr
    50                  55                  60

Asp Glu Ala Glu Ile Pro Gln Val Glu Asn Ser Val Ile Asn Ala Lys
65              70                  75                  80

Ile Ala Asp Ala Glu Ala Leu Leu Glu Lys Val Thr Asp Pro Ser Ile
                85                  90                  95

Arg Gln Asn Ala Met Glu Thr Leu Thr Gly Leu Lys Ser Ser Leu Leu
                100                 105                 110

Leu Gly Thr Lys Asp Asn Asn Thr Ile Ser Ala Glu Val Asp Ser Leu
        115                 120                 125

Leu Ala Leu Leu Lys Glu Ser Gln Pro Ala Pro Ile Gln
    130                 135                 140
```

<210> SEQ ID NO 5
<211> LENGTH: 1482
<212> TYPE: DNA
<213> ORGANISM: Streptococcus pneumoniae

<400> SEQUENCE: 5

```
atgtgggtgc cgacagcag acccgagcag cccagccccc agagcacccc cgagcccagc      60
cccagccccc agcccgcccc caaccccag cccgccccca gcaacccat cgacgagaag      120
ctggtgaagg aggccgtgag aaaggtgggc gacggctacg tgttcgagga gaacggcgtg     180
agcagataca tccccgccaa ggacctgagc gccgagaccg ccgccggcat cgacagcaag     240
ctggccaagc aggagagcct gagccacaag ctgggcgcca gaagaccga cctgcccagc     300
agcgacagag agttctacaa caaggcctac gacctgctgg ccagaatcca ccaggacctg     360
ctggacaaca agggcagaca ggtggacttc gaggccctgg acaacctgct ggagagactg     420
aaggacgtgc ccagcgacaa ggtgaagctg gtggacgaca tcctggcctt cctggccccc     480
atcagacacc ccgagagact gggcaagccc aacgcccaga tcacctacac cgacgacgag     540
atccaggtgg ccaagctggc cggcaagtac accaccgagg acggctacat cttcgacccc     600
agagacatca ccagcgacga gggcgacgcc tacgtgaccc ccacatgac ccacagccac      660
tggatcaaga aggacagcct gagcgaggcc gagagagccg ccgcccaggc ctacgccaag     720
gagaagggcc tgaccccccc cagcaccgac caccaggaca gcggcaacac cgaggccaag     780
ggcgccgagg ccatctacaa cagagtgaag gccgccaaga aggtgcccct ggacagaatg     840
ccctacaacc tgcagtacac cgtggaggtg aagaacggca gcctgatcat ccccccactac     900
gaccactacc acaacatcaa gttcgagtgg ttcgacgagg gcctgtacga ggcccccaag     960
ggctacaccc tggaggacct gctggccacc gtgaagtact acgtggagca ccccaacgag    1020
agaccccaca gcgacaacgg cttcggcaac gccagcgacc acgtgagaaa gaacaaggtg    1080
gaccaggaca gcaagcccga cgaggacaag gagcacgacg aggtgagcga gcccacccac    1140
cccgagagcg acgagaagga gaaccacgcc ggcctgaacc ccagcgccga caacctgtac    1200
aagcccagca ccgacaccga ggagaccgag gaggaggccg aggacaccac cgacgaggcc    1260
gagatccccc aggtggagaa cagcgtgatc aacgccaaga tcgccgacgc cgaggccctg    1320
ctggagaagg tgaccgaccc cagcatcaga cagaacgcca tggagaccct gaccggcctg    1380
```

| | |
|---|---|
| aagagcagcc tgctgctggg caccaaggac aacaacacca tcagcgccga ggtggacagc | 1440 |
| ctgctggccc tgctgaagga gagccagccc gcccccatcc ag | 1482 |

<210> SEQ ID NO 6
<211> LENGTH: 1503
<212> TYPE: DNA
<213> ORGANISM: Artificial Sequence
<220> FEATURE:
<223> OTHER INFORMATION: Streptococcus pneumoniae

<400> SEQUENCE: 6

| | |
|---|---|
| atgggccacc accaccacca ccactgggtg cccgacagca gacccgagca gcccagcccc | 60 |
| cagagcaccc ccgagcccag ccccagcccc cagcccgccc ccaaccccca gcccgccccc | 120 |
| agcaacccca tcgacgagaa gctggtgaag gaggccgtga aaaggtgggg cgacggctac | 180 |
| gtgttcgagg agaacggcgt gagcagatac atccccgcca aggacctgag cgccgagacc | 240 |
| gccgccggca tcgacagcaa gctggccaag caggagagcc tgagccacaa gctgggcgcc | 300 |
| aagaagaccg acctgcccag cagcgacaga gagttctaca acaaggccta cgacctgctg | 360 |
| gccagaatcc accaggacct gctggacaac aagggcagca aggtggactt cgaggccctg | 420 |
| gacaacctgc tggagagact gaaggacgtg cccagcgaca aggtgaagct ggtggacgac | 480 |
| atcctggcct tcctggcccc catcagacac cccgagagac tgggcaagcc caacgcccag | 540 |
| atcacctaca ccgacgacga gatccaggtg ccaagctgg ccggcaagta caccaccgag | 600 |
| gacggctaca tcttcgaccc cagagacatc accagcgacg agggcgacgc ctacgtgacc | 660 |
| ccccacatga cccacagcca ctggatcaag aaggacagcc tgagcgaggc cgagagagcc | 720 |
| gccgccagg cctacgccaa ggagaagggc ctgaccccc ccagcaccga ccaccaggac | 780 |
| agcggcaaca ccgaggccaa gggcgccgag gccatctaca cagagtgaa ggccgccaag | 840 |
| aaggtgcccc tggacagaat gccctacaac ctgcagtaca ccgtggaggt gaagaacggc | 900 |
| agcctgatca tcccccacta cgaccactac cacaacatca gttcgagtg gttcgacgag | 960 |
| ggcctgtacg aggcccccaa gggctacacc ctggaggacc tgctggccac cgtgaagtac | 1020 |
| tacgtggagc accccaacga gacccccac agcgacaacg gcttcggcaa cgccagcgac | 1080 |
| cacgtgagaa agaacaaggt ggaccaggac agcaagcccg acgaggacaa ggagcacgac | 1140 |
| gaggtgagcg agcccaccca ccccgagagc gacgagaagg agaaccacgc cggcctgaac | 1200 |
| cccagcgccg acaacctgta caagcccagc accgacaccg aggagaccga ggaggaggcc | 1260 |
| gaggacacca ccgacgaggc cgagatcccc caggtggaga cagcgtgat caacgccaag | 1320 |
| atcgccgacg ccgaggccct gctggagaag gtgaccgacc ccagcatcag acagaacgcc | 1380 |
| atggagaccc tgaccggcct gaagagcagc ctgctgctgg gcaccaagga caacaacacc | 1440 |
| atcagcgccg aggtggacag cctgctggcc ctgctgaagg agagccagcc cgcccccatc | 1500 |
| cag | 1503 |

<210> SEQ ID NO 7
<211> LENGTH: 495
<212> TYPE: DNA
<213> ORGANISM: Streptococcus pneumoniae

<400> SEQUENCE: 7

| | |
|---|---|
| atggtgaagt actacgtgga gcaccccaac gagagacccc acagcgacaa cggcttcggc | 60 |
| aacgccagcg accacgtgag aaagaacaag gtggaccagg acagcaagcc cgacgaggac | 120 |
| aaggagcacg acgaggtgag cgagcccacc caccccgaga gcgacgagaa ggagaaccac | 180 |

```
gccggcctga acccagcgc cgacaacctg tacaagccca gcaccgacac cgaggagacc        240
gaggaggagg ccgaggacac caccgacgag gccgagatcc ccaggtgga gaacagcgtg        300 atcaacgcca agatcgccga cgccgaggcc ctgctggaga aggtgaccga ccccagcatc        360
agacagaacg ccatggagac cctgaccggc ctgaagagca gcctgctgct gggcaccaag        420
gacaacaaca ccatcagcgc cgaggtggac agcctgctgg ccctgctgaa ggagagccag        480
cccgccccca tccag                                                        495

<210> SEQ ID NO 8
<211> LENGTH: 516
<212> TYPE: DNA
<213> ORGANISM: Artificial Sequence
<220> FEATURE:
<223> OTHER INFORMATION: Streptococcus pneumoniae

<400> SEQUENCE: 8
atgggccacc accaccacca ccacgtgaag tactacgtgg agcacccaa cgagagaccc         60 cacagcgaca acggcttcgg caacgccagc gaccacgtga aaagaacaa ggtggaccag        120 gacagcaagc ccgacgagga caaggagcac gacgaggtga gcgagcccac caccccgag        180 agcgacgaga aggagaacca cgccggcctg aaccccagcg ccgacaacct gtacaagccc       240
agcaccgaca ccgaggagac cgaggaggag ccgaggaca ccaccgacga ggccgagatc        300
ccccaggtgg agaacagcgt gatcaacgcc aagatcgccg acgccgaggc cctgctggag       360
aaggtgaccg accccagcat cagacagaac gccatggaga ccctgaccgg cctgaagagc       420
agcctgctgc tgggcaccaa ggacaacaac accatcagcg ccgaggtgga cagcctgctg       480
gccctgctga aggagagcca gcccgccccc atccag                                 516

<210> SEQ ID NO 9
<211> LENGTH: 426
<212> TYPE: DNA
<213> ORGANISM: Streptococcus pneumoniae

<400> SEQUENCE: 9
atgcacgtga aaagaacaa ggtggaccag gacagcaagc ccgacgagga caaggagcac        60
gacgaggtga gcgagcccac caccccgag agcgacgaga aggagaacca cgccggcctg       120
aaccccagcg ccgacaacct gtacaagccc agcaccgaca ccgaggagac cgaggaggag      180
gccgaggaca ccaccgacga ggccgagatc ccccaggtgg agaacagcgt gatcaacgcc     240
aagatcgccg acgccgaggc cctgctggag aaggtgaccg accccagcat cagacagaac    300
gccatggaga ccctgaccgg cctgaagagc agcctgctgc tgggcaccaa ggacaacaac   360
accatcagcg ccgaggtgga cagcctgctg gccctgctga aggagagcca gcccgccccc  420
atccag                                                                 426

<210> SEQ ID NO 10
<211> LENGTH: 447
<212> TYPE: DNA
<213> ORGANISM: Artificial Sequence
<220> FEATURE:
<223> OTHER INFORMATION: Streptococcus pneumoniae

<400> SEQUENCE: 10
atgggccacc accaccacca ccacgtg agaaagaaca aggtggacca ggacagcaag          60
cccgacgagg acaaggagca cgacgaggtg agcgagccca ccaccccga gagcgacgag       120 aaggagaacc acgccggcct gaaccccagc gccgacaacc tgtacaagcc cagcaccgac      180
```

```
accgaggaga ccgaggagga ggccgaggac accaccgacg aggccgagat cccccaggtg    240
gagaacagcg tgatcaacgc caagatcgcc gacgccgagg ccctgctgga aaggtgacc    300 gaccccagca tcagacagaa cgccatggag accctgaccg gcctgaagag cagcctgctg    360
ctgggcacca aggacaacaa caccatcagc gccgaggtgg acagcctgct ggccctgctg    420
aaggagagcc agcccgcccc catccag                                        447
```

```
<210> SEQ ID NO 11
<211> LENGTH: 52
<212> TYPE: DNA
<213> ORGANISM: Artificial Sequence
<220> FEATURE:
<223> OTHER INFORMATION: Streptococcus pneumoniae

<400> SEQUENCE: 11
ctagccatgg gacatcatca tcatcatcac tgggtaccag attcaagacc ag           52
```

```
<210> SEQ ID NO 12
<211> LENGTH: 53
<212> TYPE: DNA
<213> ORGANISM: Artificial Sequence
<220> FEATURE:
<223> OTHER INFORMATION: Streptococcus pneumoniae

<400> SEQUENCE: 12
ctagccatgg gacatcatca tcatcatcac gtcaagtact atgtcgaaca tcc          53
```

```
<210> SEQ ID NO 13
<211> LENGTH: 54
<212> TYPE: DNA
<213> ORGANISM: Artificial Sequence
<220> FEATURE:
<223> OTHER INFORMATION: Streptococcus pneumoniae

<400> SEQUENCE: 13
ctagccatgg gacatcatca tcatcatcac catgttcgta aaataaggt agac          54
```

```
<210> SEQ ID NO 14
<211> LENGTH: 33
<212> TYPE: DNA
<213> ORGANISM: Artificial Sequence
<220> FEATURE:
<223> OTHER INFORMATION: Streptococcus pneumoniae

<400> SEQUENCE: 14
tggcctcgag ttactactgt ataggagccg gtt                                33
```

```
<210> SEQ ID NO 15
<211> LENGTH: 501
<212> TYPE: PRT
<213> ORGANISM: Artificial Sequence
<220> FEATURE:
<223> OTHER INFORMATION: Streptococcus pneumoniae

<400> SEQUENCE: 15
```

Met Gly His His His His His His Trp Val Pro Asp Ser Arg Pro Glu
1               5                   10                  15

Gln Pro Ser Pro Gln Ser Thr Pro Glu Pro Ser Pro Ser Pro Gln Pro
            20                  25                  30

Ala Pro Asn Pro Gln Pro Ala Pro Ser Asn Pro Ile Asp Glu Lys Leu
        35                  40                  45

Val Lys Glu Ala Val Arg Lys Val Gly Asp Gly Tyr Val Phe Glu Glu
    50                  55                  60

```
Asn Gly Val Ser Arg Tyr Ile Pro Ala Lys Asp Leu Ser Ala Glu Thr
 65                  70                  75                  80

Ala Ala Gly Ile Asp Ser Lys Leu Ala Lys Gln Glu Ser Leu Ser His
                 85                  90                  95

Lys Leu Gly Ala Lys Lys Thr Asp Leu Pro Ser Ser Asp Arg Glu Phe
            100                 105                 110

Tyr Asn Lys Ala Tyr Asp Leu Leu Ala Arg Ile His Gln Asp Leu Leu
        115                 120                 125

Asp Asn Lys Gly Arg Gln Val Asp Phe Glu Ala Leu Asp Asn Leu Leu
    130                 135                 140

Glu Arg Leu Lys Asp Val Pro Ser Asp Lys Val Lys Leu Val Asp Asp
145                 150                 155                 160

Ile Leu Ala Phe Leu Ala Pro Ile Arg His Pro Glu Arg Leu Gly Lys
                165                 170                 175

Pro Asn Ala Gln Ile Thr Tyr Thr Asp Asp Glu Ile Gln Val Ala Lys
            180                 185                 190

Leu Ala Gly Lys Tyr Thr Thr Glu Asp Gly Tyr Ile Phe Asp Pro Arg
        195                 200                 205

Asp Ile Thr Ser Asp Glu Gly Asp Ala Tyr Val Thr Pro His Met Thr
    210                 215                 220

His Ser His Trp Ile Lys Lys Asp Ser Leu Ser Glu Ala Glu Arg Ala
225                 230                 235                 240

Ala Ala Gln Ala Tyr Ala Lys Glu Lys Gly Leu Thr Pro Pro Ser Thr
                245                 250                 255

Asp His Gln Asp Ser Gly Asn Thr Glu Ala Lys Gly Ala Glu Ala Ile
            260                 265                 270

Tyr Asn Arg Val Lys Ala Lys Lys Val Pro Leu Asp Arg Met Pro
        275                 280                 285

Tyr Asn Leu Gln Tyr Thr Val Glu Val Lys Asn Gly Ser Leu Ile Ile
    290                 295                 300

Pro His Tyr Asp His Tyr His Asn Ile Lys Phe Glu Trp Phe Asp Glu
305                 310                 315                 320

Gly Leu Tyr Glu Ala Pro Lys Gly Tyr Thr Leu Glu Asp Leu Leu Ala
                325                 330                 335

Thr Val Lys Tyr Tyr Val Glu His Pro Asn Glu Arg Pro His Ser Asp
            340                 345                 350

Asn Gly Phe Gly Asn Ala Ser Asp His Val Arg Lys Asn Lys Val Asp
        355                 360                 365

Gln Asp Ser Lys Pro Asp Glu Asp Lys Glu His Asp Glu Val Ser Glu
    370                 375                 380

Pro Thr His Pro Glu Ser Asp Glu Lys Glu Asn His Ala Gly Leu Asn
385                 390                 395                 400

Pro Ser Ala Asp Asn Leu Tyr Lys Pro Ser Thr Asp Thr Glu Glu Thr
                405                 410                 415

Glu Glu Glu Ala Glu Asp Thr Thr Asp Glu Ala Glu Ile Pro Gln Val
            420                 425                 430

Glu Asn Ser Val Ile Asn Ala Lys Ile Ala Asp Ala Glu Ala Leu Leu
        435                 440                 445

Glu Lys Val Thr Asp Pro Ser Ile Arg Gln Asn Ala Met Glu Thr Leu
    450                 455                 460

Thr Gly Leu Lys Ser Ser Leu Leu Gly Thr Lys Asp Asn Asn Thr
465                 470                 475                 480

Ile Ser Ala Glu Val Asp Ser Leu Leu Ala Leu Leu Lys Glu Ser Gln
```

Pro Ala Pro Ile Gln
            500

<210> SEQ ID NO 16
<211> LENGTH: 172
<212> TYPE: PRT
<213> ORGANISM: Artificial Sequence
<220> FEATURE:
<223> OTHER INFORMATION: Streptococcus pneumoniae

<400> SEQUENCE: 16

Met Gly His His His His His His Val Lys Tyr Tyr Val Glu His Pro
1               5                   10                  15

Asn Glu Arg Pro His Ser Asp Asn Gly Phe Gly Asn Ala Ser Asp His
            20                  25                  30

Val Arg Lys Asn Lys Val Asp Gln Asp Ser Lys Pro Asp Glu Asp Lys
        35                  40                  45

Glu His Asp Glu Val Ser Glu Pro Thr His Pro Glu Ser Asp Glu Lys
    50                  55                  60

Glu Asn His Ala Gly Leu Asn Pro Ser Ala Asp Asn Leu Tyr Lys Pro
65                  70                  75                  80

Ser Thr Asp Thr Glu Glu Thr Glu Glu Ala Glu Asp Thr Thr Asp
                85                  90                  95

Glu Ala Glu Ile Pro Gln Val Glu Asn Ser Val Ile Asn Ala Lys Ile
            100                 105                 110

Ala Asp Ala Glu Ala Leu Leu Glu Lys Val Thr Asp Pro Ser Ile Arg
        115                 120                 125

Gln Asn Ala Met Glu Thr Leu Thr Gly Leu Lys Ser Ser Leu Leu Leu
    130                 135                 140

Gly Thr Lys Asp Asn Asn Thr Ile Ser Ala Glu Val Asp Ser Leu Leu
145                 150                 155                 160

Ala Leu Leu Lys Glu Ser Gln Pro Ala Pro Ile Gln
                165                 170

<210> SEQ ID NO 17
<211> LENGTH: 149
<212> TYPE: PRT
<213> ORGANISM: Artificial Sequence
<220> FEATURE:
<223> OTHER INFORMATION: Streptococcus pneumoniae

<400> SEQUENCE: 17

Met Gly His His His His His His Val Arg Lys Asn Lys Val Asp
1               5                   10                  15

Gln Asp Ser Lys Pro Asp Glu Asp Lys Glu His Asp Glu Val Ser Glu
            20                  25                  30

Pro Thr His Pro Glu Ser Asp Glu Lys Glu Asn His Ala Gly Leu Asn
        35                  40                  45

Pro Ser Ala Asp Asn Leu Tyr Lys Pro Ser Thr Asp Thr Glu Glu Thr
    50                  55                  60

Glu Glu Ala Glu Asp Thr Thr Asp Glu Ala Glu Ile Pro Gln Val
65                  70                  75                  80

Glu Asn Ser Val Ile Asn Ala Lys Ile Ala Asp Ala Glu Ala Leu Leu
                85                  90                  95

Glu Lys Val Thr Asp Pro Ser Ile Arg Gln Asn Ala Met Glu Thr Leu
            100                 105                 110

Thr Gly Leu Lys Ser Ser Leu Leu Leu Gly Thr Lys Asp Asn Asn Thr

```
                        115                 120                 125
Ile Ser Ala Glu Val Asp Ser Leu Leu Ala Leu Leu Lys Glu Ser Gln
            130                 135                 140

Pro Ala Pro Ile Gln
145

<210> SEQ ID NO 18
<211> LENGTH: 8
<212> TYPE: PRT
<213> ORGANISM: Artificial Sequence
<220> FEATURE:
<223> OTHER INFORMATION: Streptococcus pneumoniae

<400> SEQUENCE: 18

Met Gly His His His His His His
1               5

<210> SEQ ID NO 19
<211> LENGTH: 12
<212> TYPE: PRT
<213> ORGANISM: Human immunodeficiency virus

<400> SEQUENCE: 19

Gly Tyr Gly Arg Lys Lys Arg Arg Gln Arg Arg Arg
1               5                   10

<210> SEQ ID NO 20
<211> LENGTH: 16
<212> TYPE: PRT
<213> ORGANISM: Drosophila melanogaster

<400> SEQUENCE: 20

Arg Gln Ile Lys Ile Trp Phe Gln Asn Arg Arg Met Lys Trp Lys Lys
1               5                   10                  15

<210> SEQ ID NO 21
<211> LENGTH: 16
<212> TYPE: PRT
<213> ORGANISM: Homo sapiens

<400> SEQUENCE: 21

Ser Arg Arg His His Cys Arg Ser Lys Ala Lys Arg Ser Arg His His
1               5                   10                  15

<210> SEQ ID NO 22
<211> LENGTH: 14
<212> TYPE: PRT
<213> ORGANISM: Homo sapiens

<400> SEQUENCE: 22

Gly Arg Arg His His Arg Arg Ser Lys Ala Lys Arg Ser Arg
1               5                   10

<210> SEQ ID NO 23
<211> LENGTH: 2565
<212> TYPE: DNA
<213> ORGANISM: Streptococcus pneumoniae

<400> SEQUENCE: 23
ttactactgt ataggagccg gttgactttc ttttaacaaa gccaagagac tatctacttc      60
tgctgaaata gtgttattat ctttcgttcc gagaagaaga ctacttttta gaccagtcaa    120
tgtctccata gcattttgtc taatactagg atctgttact ttttctagca aggcctccgc    180
atctgctatc ttagcgttaa taacagaatt ctctacttga ggaatttcag cctcatcgtg    240
```

```
ggtatcttca gcttcttcct ctgtctcttc cgtatcagtg cttggtttat aaagattatc      300
tgctgaagga tttaaaccag cgtgattctc ttttcatca gattcagggt gagttggctc       360
acttacttca tcatgttcct tatcttcatc aggtttactg tcttggtcta ccttatttt      420 acgaacatgg tcgctagcgt taccaaaacc attatctgaa tgcggacgtt cgtttggatg      480
ttcgacatag tacttgacag tcgccaaaag atcctcaaga gtataccct taggtgcctc      540 ataaaggcct tcgtcaaacc actcaaattt gatgttatgg taatggtcat aatgaggtat     600
gattaaacta ccgttttga cttctacagt atattgaaga ttgtaaggca tacgatcaag     660
tggcaccttc ttagctgctt tcacgcggtt gtagatagct tctgctcctt ttgcctcagt    720
atttcctgaa tcctgatggt ctgtcgaagg aggggtcaaa cctttctctt tagcataagc    780
ctgggctgcc gctctctcag cttcagacaa actatctttt ttaatccagt ggctatgggt   840
catatgtgga gttacatagg catccccctc atcactggtt atatcacgag atcaaagat    900 ataaccgtct tctgttgtgt acttgcctgc caacttggct acttgaatct catcatcagt   960
gtaggtaatt tgcgcatttg gttttcctaa acgttctgga tgacgaatcg gagctaagaa  1020
ggcaagaata tcatccacta acttgacttt atcacttggg acatccttga gtcgttccaa  1080
caggttatcc aaagcctcaa atcaacttg tcgacccttta ttatcaagta aatcttggtg 1140
aattcttgct agtaagtcat aagccttatt gtaaaattct cgatcactag atgggaggtc  1200
agttttctta gctcctagct tatgagataa acttcctgc ttggccagtt tgctatcaat   1260
gcctgctgct gtttctgctg aaagatcctt ggctgggata taacgagaaa ctccattctc  1320
ctcaaagaca taaccatcgc ctacttttcg aacagcttct ttgaccaatt tctcatcaat  1380
tggattgctt ggagctggtt gaggatttgg tgcaggttgc ggacttggac taggttccgg   1440
agtcgattgt ggacttggtt gttctggtct tgaatctggt acccaatggt ttgaacgata  1500
acgaagggga ataatacgag caattcgttt ttccaattca gacatttgtt cataagggat  1560
aaagtggtaa tggttaccat gagggacagc tacacctctg gcggttcgac ttgtgatttg  1620
cgctgggtcg aaaataaggc catcagattc cacatggcgt tctgataagg gtttagcata  1680
caattcacgt aaaaggcttg aaatgttttc cccttgatt tgatgataag ttggagtgac   1740
agtcagattg tggttctctg acaatcttgg ttgagctgga tttgcattat aactagaact  1800
tgaagaagga cgagatccct gcttcccatt ccaataggct tctgcagcag ctaactcgct   1860
agctgataac tcattcttag gaatgtaatg gtaatggtcg ccgtgaggaa cgatataagc   1920
atcacccgtg tcctcaatga tatcagatgc attgaagata taaccatcat ccgttgtata  1980
gcgtccttgg gctctggctg caactactgc ttgatcgtta gaaccacccc cgtgattatg  2040
actgtgttcc tgcttctgac gtttaatctc ttcttttgtc cgaatattat ccgcatgagc  2100
tgcatcctta aggtaaacat agtattttcc atctaccttg ataacataac cacccttgat  2160
ttcattgaca atgtctgaat ccttcaactg ataattcgga tctttcatga ggagctcttc  2220
actgatgatg gcatcataag ggaccttgcc attatagtaa tgataatggt ctccatgaga  2280
ggtcacataa ccttgatccg taatcttgat gacgatttgt tcggcgttga tcccctccct  2340
cttactgact tcatctggtg tcaagttttc tgccttttga ccagcctgat caccatctat  2400
ataagaaact cgattagact cttctttaac ctgaccagct tggtgacgac caagttcata  2460
ggaagatccg cgacccattt gctgtccacc agtcatgcta gccatatggc tgccgcgcgg  2520
caccaggccg ctgctgtgat gatgatgatg atggctgctg cccat                   2565
```

<210> SEQ ID NO 24
<211> LENGTH: 853
<212> TYPE: PRT
<213> ORGANISM: Streptococcus pneumoniae

<400> SEQUENCE: 24

```
Met Gly Ser Ser His His His His His His Ser Ser Gly Leu Val Pro
1               5                   10                  15

Arg Gly Ser His Met Ala Ser Met Thr Gly Gly Gln Gln Met Gly Arg
            20                  25                  30

Gly Ser Ser Tyr Glu Leu Gly Arg His Gln Ala Gly Gln Val Lys Lys
        35                  40                  45

Glu Ser Asn Arg Val Ser Tyr Ile Asp Gly Asp Gln Ala Gly Gln Lys
    50                  55                  60

Ala Glu Asn Leu Thr Pro Asp Glu Val Ser Lys Arg Glu Gly Ile Asn
65                  70                  75                  80

Ala Glu Gln Ile Val Ile Lys Ile Thr Asp Gln Gly Tyr Val Thr Ser
                85                  90                  95

His Gly Asp His Tyr His Tyr Tyr Asn Gly Lys Val Pro Tyr Asp Ala
            100                 105                 110

Ile Ile Ser Glu Glu Leu Leu Met Lys Asp Pro Asn Tyr Gln Leu Lys
        115                 120                 125

Asp Ser Asp Ile Val Asn Glu Ile Lys Gly Gly Tyr Val Ile Lys Val
    130                 135                 140

Asp Gly Lys Tyr Tyr Val Tyr Leu Lys Asp Ala Ala His Ala Asp Asn
145                 150                 155                 160

Ile Arg Thr Lys Glu Glu Ile Lys Arg Gln Lys Gln Glu His Ser His
                165                 170                 175

Asn His Gly Gly Gly Ser Asn Asp Gln Ala Val Val Ala Ala Arg Ala
            180                 185                 190

Gln Gly Arg Tyr Thr Thr Asp Asp Gly Tyr Ile Phe Asn Ala Ser Asp
        195                 200                 205

Ile Ile Glu Asp Thr Gly Asp Ala Tyr Ile Val Pro His Gly Asp His
    210                 215                 220

Tyr His Tyr Ile Pro Lys Asn Glu Leu Ser Ala Ser Glu Leu Ala Ala
225                 230                 235                 240

Ala Glu Ala Tyr Trp Asn Gly Lys Gln Gly Ser Arg Pro Ser Ser Ser
                245                 250                 255

Ser Ser Tyr Asn Ala Asn Pro Ala Gln Pro Arg Leu Ser Glu Asn His
            260                 265                 270

Asn Leu Thr Val Thr Pro Thr Tyr His Gln Asn Gln Gly Glu Asn Ile
        275                 280                 285

Ser Ser Leu Leu Arg Glu Leu Tyr Ala Lys Pro Leu Ser Glu Arg His
    290                 295                 300

Val Glu Ser Asp Gly Leu Ile Phe Asp Pro Ala Gln Ile Thr Ser Arg
305                 310                 315                 320

Thr Ala Arg Gly Val Ala Val Pro His Gly Asn His Tyr His Phe Ile
                325                 330                 335

Pro Tyr Glu Gln Met Ser Glu Leu Glu Lys Arg Ile Ala Arg Ile Ile
            340                 345                 350

Pro Leu Arg Tyr Arg Ser Asn His Trp Val Pro Asp Ser Arg Pro Glu
        355                 360                 365

Gln Pro Ser Pro Gln Ser Thr Pro Glu Pro Ser Pro Ser Gln Pro
    370                 375                 380

Ala Pro Asn Pro Gln Pro Ala Pro Ser Asn Pro Ile Asp Glu Lys Leu
```

```
                385                 390                 395                 400
            Val Lys Glu Ala Val Arg Lys Val Gly Asp Gly Tyr Val Phe Glu Glu
                            405                 410                 415

Asn Gly Val Ser Arg Tyr Ile Pro Ala Lys Asp Leu Ser Ala Glu Thr
                        420                 425                 430

Ala Ala Gly Ile Asp Ser Lys Leu Ala Lys Gln Glu Ser Leu Ser His
                        435                 440                 445

Lys Leu Gly Ala Lys Thr Asp Leu Pro Ser Asp Arg Glu Phe
                450                 455                 460

Tyr Asn Lys Ala Tyr Asp Leu Leu Ala Arg Ile His Gln Asp Leu Leu
            465                 470                 475                 480

Asp Asn Lys Gly Arg Gln Val Asp Phe Glu Ala Leu Asp Asn Leu Leu
                            485                 490                 495

Glu Arg Leu Lys Asp Val Pro Ser Asp Lys Val Lys Leu Val Asp Asp
                        500                 505                 510

Ile Leu Ala Phe Leu Ala Pro Ile Arg His Pro Glu Arg Leu Gly Lys
                        515                 520                 525

Pro Asn Ala Gln Ile Thr Tyr Thr Asp Asp Glu Ile Gln Val Ala Lys
                        530                 535                 540

Leu Ala Gly Lys Tyr Thr Thr Glu Asp Gly Tyr Ile Phe Asp Pro Arg
            545                 550                 555                 560

Asp Ile Thr Ser Asp Glu Gly Asp Ala Tyr Val Thr Pro His Met Thr
                            565                 570                 575

His Ser His Trp Ile Lys Lys Asp Ser Leu Ser Glu Ala Glu Arg Ala
                        580                 585                 590

Ala Ala Gln Ala Tyr Ala Lys Glu Lys Gly Leu Thr Pro Pro Ser Thr
                        595                 600                 605

Asp His Gln Asp Ser Gly Asn Thr Glu Ala Lys Gly Ala Glu Ala Ile
                        610                 615                 620

Tyr Asn Arg Val Lys Ala Ala Lys Lys Val Pro Leu Asp Arg Met Pro
            625                 630                 635                 640

Tyr Asn Leu Gln Tyr Thr Val Glu Val Lys Asn Gly Ser Leu Ile Ile
                            645                 650                 655

Pro His Tyr Asp His Tyr His Asn Ile Lys Phe Glu Trp Phe Asp Glu
                        660                 665                 670

Gly Leu Tyr Glu Ala Pro Lys Gly Tyr Thr Leu Glu Asp Leu Leu Ala
                        675                 680                 685

Thr Val Lys Tyr Tyr Val Glu His Pro Asn Gly Arg Pro His Ser Asp
            690                 695                 700

Asn Gly Phe Gly Asn Ala Ser Asp His Val Arg Lys Asn Lys Val Asp
            705                 710                 715                 720

Gln Asp Ser Lys Pro Asp Glu Asp Lys Glu His Asp Glu Val Ser Glu
                        725                 730                 735

Pro Thr His Pro Glu Ser Asp Glu Lys Glu Asn His Ala Gly Leu Asn
                        740                 745                 750

Pro Ser Ala Asp Asn Leu Tyr Lys Pro Ser Thr Asp Thr Glu Glu Thr
                        755                 760                 765

Glu Glu Glu Ala Glu Asp Thr Thr Asp Glu Ala Glu Ile Pro Gln Val
                770                 775                 780

Glu Asn Ser Val Ile Asn Ala Lys Ile Ala Asp Ala Glu Ala Leu Leu
            785                 790                 795                 800

Glu Lys Val Thr Asp Pro Ser Ile Arg Gln Asn Ala Met Glu Thr Leu
                            805                 810                 815
```

-continued

Thr Gly Leu Lys Ser Ser Leu Leu Gly Thr Lys Asp Asn Asn Thr
            820                 825                 830

Ile Ser Ala Glu Val Asp Ser Leu Ala Leu Leu Lys Glu Ser Gln
            835                 840                 845

Pro Ala Pro Ile Gln
    850

<210> SEQ ID NO 25
<211> LENGTH: 843
<212> TYPE: PRT
<213> ORGANISM: Streptococcus pneumoniae

<400> SEQUENCE: 25

Ser Ser Gly Leu Val Pro Arg Gly Ser His Met Ala Ser Met Thr Gly
1               5                   10                  15

Gly Gln Gln Met Gly Arg Gly Ser Ser Tyr Glu Leu Gly Arg His Gln
                20                  25                  30

Ala Gly Gln Val Lys Lys Glu Ser Asn Arg Val Ser Tyr Ile Asp Gly
            35                  40                  45

Asp Gln Ala Gly Gln Lys Ala Glu Asn Leu Thr Pro Asp Glu Val Ser
        50                  55                  60

Lys Arg Glu Gly Ile Asn Ala Glu Gln Ile Val Ile Lys Ile Thr Asp
65                  70                  75                  80

Gln Gly Tyr Val Thr Ser His Gly Asp His Tyr His Tyr Tyr Asn Gly
                85                  90                  95

Lys Val Pro Tyr Asp Ala Ile Ile Ser Glu Glu Leu Leu Met Lys Asp
            100                 105                 110

Pro Asn Tyr Gln Leu Lys Asp Ser Asp Ile Val Asn Glu Ile Lys Gly
        115                 120                 125

Gly Tyr Val Ile Lys Val Asp Gly Lys Tyr Tyr Val Tyr Leu Lys Asp
    130                 135                 140

Ala Ala His Ala Asp Asn Ile Arg Thr Lys Glu Glu Ile Lys Arg Gln
145                 150                 155                 160

Lys Gln Glu His Ser His Asn His Gly Gly Gly Ser Asn Asp Gln Ala
                165                 170                 175

Val Val Ala Ala Arg Ala Gln Gly Arg Tyr Thr Thr Asp Asp Gly Tyr
            180                 185                 190

Ile Phe Asn Ala Ser Asp Ile Ile Glu Asp Thr Gly Asp Ala Tyr Ile
        195                 200                 205

Val Pro His Gly Asp His Tyr His Tyr Ile Pro Lys Asn Glu Leu Ser
    210                 215                 220

Ala Ser Glu Leu Ala Ala Ala Glu Ala Tyr Trp Asn Gly Lys Gln Gly
225                 230                 235                 240

Ser Arg Pro Ser Ser Ser Ser Tyr Asn Ala Asn Pro Ala Gln Pro
                245                 250                 255

Arg Leu Ser Glu Asn His Asn Leu Thr Val Thr Pro Thr Tyr His Gln
            260                 265                 270

Asn Gln Gly Glu Asn Ile Ser Ser Leu Leu Arg Glu Leu Tyr Ala Lys
        275                 280                 285

Pro Leu Ser Glu Arg His Val Glu Ser Asp Gly Leu Ile Phe Asp Pro
    290                 295                 300

Ala Gln Ile Thr Ser Arg Thr Ala Arg Gly Val Ala Val Pro His Gly
305                 310                 315                 320

Asn His Tyr His Phe Ile Pro Tyr Glu Gln Met Ser Glu Leu Glu Lys
                325                 330                 335

```
Arg Ile Ala Arg Ile Ile Pro Leu Arg Tyr Arg Ser Asn His Trp Val
            340                 345                 350

Pro Asp Ser Arg Pro Glu Gln Pro Ser Pro Gln Ser Thr Pro Glu Pro
            355                 360                 365

Ser Pro Ser Pro Gln Pro Ala Pro Asn Pro Gln Pro Ala Pro Ser Asn
370                 375                 380

Pro Ile Asp Glu Lys Leu Val Lys Glu Ala Val Arg Lys Val Gly Asp
385                 390                 395                 400

Gly Tyr Val Phe Glu Glu Asn Gly Val Ser Arg Tyr Ile Pro Ala Lys
                405                 410                 415

Asp Leu Ser Ala Glu Thr Ala Ala Gly Ile Asp Ser Lys Leu Ala Lys
            420                 425                 430

Gln Glu Ser Leu Ser His Lys Leu Gly Ala Lys Lys Thr Asp Leu Pro
            435                 440                 445

Ser Ser Asp Arg Glu Phe Tyr Asn Lys Ala Tyr Asp Leu Leu Ala Arg
450                 455                 460

Ile His Gln Asp Leu Leu Asp Asn Lys Gly Arg Gln Val Asp Phe Glu
465                 470                 475                 480

Ala Leu Asp Asn Leu Leu Glu Arg Leu Lys Asp Val Pro Ser Asp Lys
                485                 490                 495

Val Lys Leu Val Asp Asp Ile Leu Ala Phe Leu Ala Pro Ile Arg His
            500                 505                 510

Pro Glu Arg Leu Gly Lys Pro Asn Ala Gln Ile Thr Tyr Thr Asp Asp
            515                 520                 525

Glu Ile Gln Val Ala Lys Leu Ala Gly Lys Tyr Thr Thr Glu Asp Gly
            530                 535                 540

Tyr Ile Phe Asp Pro Arg Asp Ile Thr Ser Asp Glu Gly Asp Ala Tyr
545                 550                 555                 560

Val Thr Pro His Met Thr His Ser His Trp Ile Lys Lys Asp Ser Leu
                565                 570                 575

Ser Glu Ala Glu Arg Ala Ala Ala Gln Ala Tyr Ala Lys Glu Lys Gly
            580                 585                 590

Leu Thr Pro Pro Ser Thr Asp His Gln Asp Ser Gly Asn Thr Glu Ala
            595                 600                 605

Lys Gly Ala Glu Ala Ile Tyr Asn Arg Val Lys Ala Ala Lys Lys Val
610                 615                 620

Pro Leu Asp Arg Met Pro Tyr Asn Leu Gln Tyr Thr Val Glu Val Lys
625                 630                 635                 640

Asn Gly Ser Leu Ile Ile Pro His Tyr Asp His Tyr His Asn Ile Lys
                645                 650                 655

Phe Glu Trp Phe Asp Glu Gly Leu Tyr Glu Ala Pro Lys Gly Tyr Thr
            660                 665                 670

Leu Glu Asp Leu Leu Ala Thr Val Lys Tyr Tyr Val Glu His Pro Asn
            675                 680                 685

Glu Arg Pro His Ser Asp Asn Gly Phe Gly Asn Ala Ser Asp His Val
690                 695                 700

Arg Lys Asn Lys Val Asp Gln Asp Ser Lys Pro Asp Glu Asp Lys Glu
705                 710                 715                 720

His Asp Glu Val Ser Glu Pro Thr His Pro Glu Ser Asp Glu Lys Glu
                725                 730                 735

Asn His Ala Gly Leu Asn Pro Ser Ala Asp Asn Leu Tyr Lys Pro Ser
            740                 745                 750

Thr Asp Thr Glu Glu Thr Glu Glu Glu Ala Glu Asp Thr Thr Asp Glu
            755                 760                 765
```

```
Ala Glu Ile Pro Gln Val Glu Asn Ser Val Ile Asn Ala Lys Ile Ala
        770             775                 780

Asp Ala Glu Ala Leu Leu Glu Lys Val Thr Asp Pro Ser Ile Arg Gln
785             790                 795                     800

Asn Ala Met Glu Thr Leu Thr Gly Leu Lys Ser Ser Leu Leu Leu Gly
                805                 810                 815

Thr Lys Asp Asn Asn Thr Ile Ser Ala Glu Val Asp Ser Leu Leu Ala
            820                 825                 830

Leu Leu Lys Glu Ser Gln Pro Ala Pro Ile Gln
        835                 840

<210> SEQ ID NO 26
<211> LENGTH: 101
<212> TYPE: PRT
<213> ORGANISM: Streptococcus pneumoniae

<400> SEQUENCE: 26

His Val Arg Lys Asn Lys Val Asp Gln Asp Ser Lys Pro Asp Glu Asp
1               5                   10                  15

Lys Glu His Asp Glu Val Ser Glu Pro Thr His Pro Glu Ser Asp Glu
                20                  25                  30

Lys Glu Asn His Ala Gly Leu Asn Pro Ser Ala Asp Asn Leu Tyr Lys
            35                  40                  45

Pro Ser Thr Asp Thr Glu Glu Thr Glu Glu Glu Ala Glu Asp Thr Thr
        50                  55                  60

Asp Glu Ala Glu Ile Pro Gln Val Glu Asn Ser Val Ile Asn Ala Lys
65                  70                  75                  80

Ile Ala Asp Ala Glu Ala Leu Leu Glu Lys Val Thr Asp Pro Ser Ile
                85                  90                  95

Arg Gln Asn Ala Met
                100
```

IMMUNOGENIC POLYPEPTIDES AND MONOCLONAL ANTIBODIES

RELATED APPLICATION

This application is the National Stage Application under 35 U.S.C. §371 of International Application No. PCT/CA2008/001353 filed Jul. 23, 2008, which claims priority to U.S. Provisional Application No. 60/961,723 filed Jul. 23, 2007. Both applications are incorporated herein by reference in their entirety.

TECHNICAL FIELD

This invention relates to immunology, and more particularly to eliciting an immune response to bacteria.

BACKGROUND

*Streptococcus pneumoniae* is a rather ubiquitous human pathogen, which can infect several organs including the lungs, the central nervous system (CNS), the middle ear, and the nasal tract. Infection results in various symptoms such as bronchitis, pneumonia, meningitis, sinus infection, and sepsis. *S. pneumoniae* is a major cause of bacterial meningitis in humans and is associated with significant mortality and morbidity despite antibiotic treatment (Quagliarello et al., (1992) N. Eng. J. Med. 327: 869-872).

There are two currently available pneumococcal vaccines. One is a vaccine for adults composed of 23 different capsular polysaccharides which together represent the capsular types of about 90% of strains causing pneumococcal infection. This vaccine, however, is not immunogenic in children, an age group with high susceptibility to pneumococcal infection. In adults the vaccine has been shown to be about 60% efficacious against bacteremic pneumonia, but it is less efficacious in adults at higher risk of pneumococcal infection because of age or underlying medical conditions (Fedson, and Musher. 2004. "Pneumococcal Polysaccharide Vaccine", pp. 529-588. In *Vaccines*. S. A. Plotkin and W. A. Orenstein (eds.), W. B. Saunders and Co., Philadelphia, Pa.; Shapiro et al., *N. Engl. J. Med.* 325:1453-1460 (1991)). This vaccine has not been shown to be effective against non-bacteremic pneumococcal pneumonia, the most common form of infection.

The second available vaccine is a 7-valent conjugate vaccine that is efficacious against bacteremic pneumococcal infections in children less than 2 years of age. It has also demonstrated efficacy against pneumonia (Black et al., *Arch. Pediatr.* 11(7):485-489 (2004)). The production of this vaccine is complicated because of the need to produce 7 different conjugates and this leads to the vaccine being expensive (about $200/child). Moreover, the vaccine does not do a good job of covering infections in the developing world where non-vaccine types of *Streptococcus pneumoniae* are very common (Di Fabio et al., *Pediatr. Infect. Dis. J.* 20:959-967 (2001); Mulholland, *Trop. Med. Int. Health* 10:497-500 (2005)). This vaccine does not work as well against otitis media and colonization as it does against invasive disease. It has also been shown that the use of the 7-valent conjugate vaccine has led to an increase in colonization and disease with strains of capsule types not represented by the 7 polysaccharides included in the vaccine (Bogaert et al., *Lancet Infect. Dis.* 4:144-154 (2004); Eskola et al., *N Engl. J. Med.* 344:403-409 (2001); Mbelle et al., *J. Infect. Dis.* 180:1171-1176 (1999)). Therefore, a need remains for effective treatments for *Streptococcus pneumoniae*.

SUMMARY

Compositions and methods for eliciting an immune response against *Streptococcus pneumoniae* are described. Immunogenic pneumococcal histidine triad protein D (PhtD) polypeptides, and in particular fragments, derivatives and variants thereof, as well as nucleic acids encoding the same, are provided. Monoclonal antibodies (and hybridomas producing the same) having specificity for such polypeptides, fragments, derivatives or variants are also provided. Further provided are methods of making and using the immunogenic polypeptides, derivatives, variants and monoclonal antibodies.

The present invention provides an isolated nucleic acid selected from the group consisting of: a) a nucleic acid encoding a *S.pneumonaie* polypeptide having at least 90% identity to SEQ ID NO:2; b) a nucleic acid fully complementary to a nucleic acid encoding a *S. pneumonaie* polypeptide having at least 90% identity to SEQ ID NO:2; and c) an RNA of (a) or (b), wherein U is substituted for T.

According to a preferred embodiment of the present invention, the sequence identity is at least 85%, 90% and more preferably 95 to 100%.

The present invention also provides an isolated polypeptide comprising an amino acid sequence having at least 80%, 85%, 90%, 95% or 100% identity to SEQ ID NO:2 and a monoclonal antibody which specifically binds to a polypeptide having at least 80%, 85%, 90%, 95% or 100% identity to SEQ ID NO:2.

In accordance with another aspect of the invention, provided is an isolated nucleic acid selected from the group consisting of: a) a nucleic acid encoding a *S. pneumonaie* polypeptide having at least 80% identity to SEQ ID NO:3; b) a nucleic acid fully complementary to a nucleic acid encoding a *S. pneumonaie* polypeptide having at least 80% identity to SEQ ID NO:3; and c) an RNA of (a) or (b), wherein U is substituted for T.

According to a preferred embodiment of the present invention, the sequence identity is at least 85%, 90% and more preferably 95 to 100%.

The present invention also provides an isolated polypeptide comprising an amino acid sequence having at least 80%, 85%, 90%, 95% or 100% identity to SEQ ID NO:3 and also a monoclonal antibody which specifically binds to a polypeptide having at least 80%, 85%, 90%, 95% or 100% identity to SEQ ID NO:3.

In accordance with another aspect of the invention, provided is an isolated nucleic acid selected from the group consisting of: a) a nucleic acid encoding a S.pneumonaie polypeptide having at least 80% identity to SEQ ID NO:4; b) a nucleic acid fully complementary to a nucleic acid encoding a S.pneumonaie polypeptide having at least 80% identity to SEQ ID NO:4; and c) an RNA of (a) or (b), wherein U is substituted for T.

According to a preferred embodiment of the present invention, the sequence identity is at least 85%, 90% and more preferably 95 to 100%.

The present invention also provides an isolated polypeptide comprising an amino acid sequence having at least 80%, 85%, 90%, 95% or 100% identity to SEQ ID NO:4 and also a monoclonal antibody that specifically binds to a polypeptide having at least 80%, 85%, 90%, 95% or 100% identity to SEQ ID NO:4.

According to a further aspect of the invention, provided is a monoclonal antibody which specifically binds to an antigenic determinant of a peptide having an amino acid sequence as set out in SEQ ID NO:4.

In accordance with a preferred embodiment of the present invention, the antigenic determinant to which the monoclonal antibody specifically binds, is positioned in a peptide having an amino acid sequence as set out in SEQ ID NO:4 in a region spanning amino acid 1 and amino acid 101.

The present invention also provides an immunogenic fragment selected from the group consisting of SEQ ID NO.: 2, SEQ ID NO.: 3, and SEQ ID NO.: 4 or a variant thereof selected from the group consisting of SEQ ID NO.: 15, SEQ ID NO.: 16, and SEQ ID NO.: 17.

In accordance with another aspect of the present invention also provided is a method for immunizing a host against infection by and a method for treating an infection by a *Streptococcus* sp. bacteria comprising administering to the host at least one polypeptide of PhtD selected from the group consisting of SEQ ID NO.: 2, SEQ ID NO.: 3, and SEQ ID NO.: 4 or a variant thereof selected from the group consisting of SEQ ID NO.: 15, SEQ ID NO.: 16, and SEQ ID NO.: 17.

In accordance with a further aspect of the present invention, a monoclonal antibody is provided.

The present invention also provides a method for preventing infection by, and a method for treating an infection by, a *Streptococcus* sp. bacteria in a host comprising administering to the host at least one monoclonal antibody.

In a preferred embodiment of the invention, at least two monoclonal antibodies are administered to prevent infection and/or to treat infection by a *Streptococcus* sp. bacteria.

In accordance with another aspect of the present invention, provided is a method for determining the amount of a protein in a biological sample, comprising exposing a test biological sample to a monoclonal antibody or a derivative thereof, measuring the amount of antibody or derivative bound to the sample, and comparing the amount of binding in the test biological sample to the amount of binding observed in a control biological sample, wherein increased binding in the test biological sample relative to the control biological sample indicates the presence of the protein therein.

Accordance with a further aspect of the present invention, provided is a method for detecting a *Streptococcus* sp. bacteria or protein thereof in a biological sample, the method comprising the steps of:
(a) exposing a test biological sample to at least one a monoclonal antibody or derivative thereof, under conditions allowing for the antibody to a component of the sample for which is has specificity; and,
(b) determining the amount of antibody bound to components of the test biological sample; and,
(c) comparing the amount of antibody bound to the test biological sample to the amount bound to a control sample;
wherein the binding of a significantly greater amount of antibody to components of the test biological sample as compared to the control biological sample indicates the presence of *Streptococcus* sp. bacteria or a protein thereof in the sample.

Also provided by the present invention is a kit for detecting *Streptococcus* sp. bacteria or a protein thereof in a biological sample, the kit comprising at least one monoclonal antibody or a derivative thereof, and instructions for use.

In addition to the exemplary aspects and embodiments described above, further aspect and embodiments will become apparent by references to the study of the following detailed descriptions.

DETAILED DESCRIPTION

Disclosed herein are polypeptides and nucleic acids useful as immunological agents or tools for identifying the binding sites for monoclonal antibodies, absorbing out cross-reactive antibodies from polyclonal sera, defining regions of PhtD encompassing protective epitopes, characterizing the human immune response (in clinical trials) at higher resolution than that afforded by the full-length protein, and that may provide advantage during manufacturing. As test reagents, this collection of truncated proteins will allow for characterization of the individual contribution of PhtD to a multivalent vaccine.

In one embodiment, compositions and methodologies useful for treating and/or preventing conditions relating to the presence of organisms expressing PhtD such as *Streptococcus* sp. bacteria, by stimulating an immune response against PhtD and thereby treating the organism. The immune response is shown to occur following administration of PhtD, an immunogenic fragment thereof, or a variant thereof, or a nucleic acid encoding any of the same, to a host. In such cases, PhtD, the immunogenic fragment thereof, or the variant thereof acts as an immunogen. As used herein, an "immunogen" is a polypeptide, peptide, fragment, or variant thereof, each being derived from PhtD that produces an immune response in a host to which the immunogen has been administered. The immune response may include the production of antibodies that bind to at least one epitope of the immunogen and/or the generation of a cellular immune response against cells expressing an epitope of the immunogen. The response may be detected as, for instance, an enhancement of an existing immune response against the immunogen by, for example, detecting an increased antibody response (i.e., amount of antibody, increased affinity/avidity) or an increased cellular response (i.e., increased number of activated T cells, increased affinity/avidity of T cell receptors). Other measures of an immune response are known in the art and could be utilized to determine the presence of an immune response in the host. Standard methodologies are available in the art for making these determinations. In certain embodiments, the immune response is detectable but not necessarily protective. In such cases, the composition comprising the immunogen may be considered an immunological composition. In certain embodiments, the immune response is protective, meaning the immune response is capable of preventing the growth of or eliminating from the host the PhtD expressing organism (i.e., *Streptococcus* sp.). In such cases, the composition comprising the immunogen, while still being considered an immunological composition, may be additionally referred to as a vaccine. In certain embodiments, multiple immunogens are utilized in a single composition.

Immunogenic fragments (i.e., immunogens) of PhtD are described herein along with methods of making and using the fragments. Immunogens described herein include polypeptides comprising full-length PhtD (with or without the signal sequence), PhtD fragments thereof, and variants thereof. It is preferred that the amino acid sequences utilized are derived from *Streptococcus pneumoniae* PhtD (GenBank Accession No. AF318955; Adamou, et al. Infect. Immun. 69 (2), 949-958 (2001)) having the amino acid sequence shown below:

(SEQ ID NO. 1)
MKINKKYLAGSVAVLALSVCSYELGRHQAGQVKKESNRVSYIDGDQAGQK

AENLTPDEVSKREGINAEQIVIKITDQGYVTSHGDHYHYYNGKVPYDAII

SEELLMKDPNYQLKDSDIVNEIKGGYVIKVDGKYYVYLKDAAHADNIRTK

EEIKRQKQEHSHNHGGGSNDQAVVAARAQGRYTTDDGYIFNASDIIEDTG

DAYIVPHGDHYHYIPKNELSASELAAAEAYWNGKQGSRPSSSSSYNANPA

QPRLSENHNLTVTPTYHQNQGENISSLLRELYAKPLSERHVESDGLIFDP

-continued
AQITSRTARGVAVPHGNHYHFIPYEQMSELEKRIARIIPLRYRSNHWVPD

SRPEQPSPQSTPEPSPSPQPAPNPQPAPSNPIDEKLVKEAVRKVGDGYVF

EENGVSRYIPAKDLSAETAAGIDSKLAKQESLSHKLGAKKTDLPSSDREF

YNKAYDLLARIHQDLLDNKGRQVDFEALDNLLERLKDVPSDKVKLVDDIL

AFLAPIRHPERLGKPNAQITYTDDEIQVAKLAGKYTTEDGYIFDPRDITS

DEGDAYVTPHMTHSHWIKKDSLSEAERAAAQAYAKEKGLTPPSTDHQDSG

NTEAKGAEAIYNRVKAAKKVPLDRMPYNLQYTVEVKNGSLIIPHYDHYHN

IKFEWFDEGLYEAPKGYTLEDLLATVKYYVEHPNERPHSDNGFGNASDHV

RKNKVDQDSKPDEDKEHDEVSEPTHPESDEKENHAGLNPSADNLYKPSTD

TEETEEEAEDTTDEAEIPQVENSVINAKIADAEALLEKVTDPSIRQNAME

TLTGLKSSLLLGTKDNNTISAEVDSLLALLKESQPAPIQ

Preferred immunogenic compositions comprise one or more polypeptides having the amino acid sequence of SEQ ID NOS. 2, 3, 4, 15, 16 or 17, for example. These polypeptides may include one or more conservative amino acid substitutions and/or a signal sequence and/or a detectable "tag" such as His (i.e., MGHHHHHH (SEQ ID NO. 18); see for example, SEQ ID NOS. 15-17). Exemplary, preferred immunogenic fragments include:

TRUNCATION 1
(SEQ ID NO. 2)
WVPDSRPEQPSPQSTPEPSPSPQPAPNPQPAPSNPIDEKLVKEAVRKVGD

GYVFEENGVSRYIPAKDLSAETAAGIDSKLAKQESLSHKLGAKKTDLPSS

DREFYNKAYDLLARIHQDLLDNKGRQVDFEALDNLLERLKDVPSDKVKLV

DDILAFLAPIRHPERLGKPNAQITYTDDEIQVAKLAGKYTTEDGYIFDPR

DITSDEGDAYVTPHMTHSHWIKKDSLSEAERAAAQAYAKEKGLTPPSTDH

QDSGNTEAKGAEAIYNRVKAAKKVPLDRMPYNLQYTVEVKNGSLIIPHYD

HYHNIKFEWFDEGLYEAPKGYTLEDLLATVKYYVEHPNERPHSDNGFGNA

SDHVRKNKVDQDSKPDEDKEHDEVSEPTHPESDEKENHAGLNPSADNLYK

PSTDTEETEEEAEDTTDEAEIPQVENSVINAKIADAEALLEKVTDPSIRQ

NAMETLTGLKSSLLLGTKDNNTISAEVDSLLALLKESQPAPIQ;

TRUNCATION 2
(SEQ ID NO. 3)
VKYYVEHPNERPHSDNGFGNASDHVRKNKVDQDSKPDEDKEHDEVSEPTH

PESDEKENHAGLNPSADNLYKPSTDTEETEEEAEDTTDEAEIPQVENSVI

NAKIADAEALLEKVTDPSIRQNAMETLTGLKSSLLLGTKDNNTISAEVDS

LLALLKESQPAPIQ;
and,

TRUNCATION 3
(SEQ ID NO. 4)
HVRKNKVDQDSKPDEDKEHDEVSEPTHPESDEKENHAGLNPSADNLYKPS

TDTEETEEEAEDTTDEAEIPQVENSVINAKIADAEALLEKVTDPSIRQNA

METLTGLKSSLLLGTKDNNTISAEVDSLLALLKESQPAPIQ.

As mentioned above, immunogenic polypeptides provided herein may comprise one or more conservative amino acid substitutions to the immunogenic PhtD polypeptides (i.e., SEQ ID NOS. 2, 3, and/or 4). For instance, immunogens provided herein may comprise a C-terminal portion of the naturally occurring PhtD with one or more amino acid sequence modifications such that about 60 to about 99% sequence identity or similarity to the naturally occurring PhtD is maintained. Exemplary variants have amino acid sequences that are about 60 to about 99%, about 60 to about 65%, about 65 to about 70%, about 70 to about 75%, about 80 to about 85%, about 85 to about 90%, about 90 to about 99%, or about 95 to about 99% similar or identical to SEQ ID NOS. 2, 3, 4, 15, 16 and/or 17, and/or any fragments or derivatives thereof Variants are preferably selected for their ability to function as immunogens using the methods taught herein or those available in the art.

Suitable amino acid sequence modifications include substitutional, insertional, deletional or other changes to the amino acids of any of the PhtD polypeptides discussed herein. Substitutions, deletions, insertions or any combination thereof may be combined in a single variant so long as the variant is an immunogenic polypeptide. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known and include, but are not limited to, M13 primer mutagenesis and PCR mutagenesis. Amino acid substitutions are typically of single residues, but can occur at a number of different locations at once. Substitutional variants are those in which at least one residue has been removed and a different residue inserted in its place. Such substitutions generally are made in accordance with the following Table 1 and are referred to as conservative substitutions and generally have little or no effect on the size, polarity, charge, hydrophobicity, or hydrophilicity of the amino acid residue at that position and, in particlar, do not result in decreased immunogenicity. However, others are well known to those of skill in the art.

TABLE 1

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

Variants as used herein may also include naturally occurring PhtD alleles from alternate *Streptococcus* strains that exhibit polymorphisms at one or more sites within the homologous PhtD gene. Variants can be produced by conventional molecular biology techniques. The variants are described herein relative to sequence similarity or identity as compared to the naturally occuring gene. Those of skill in the art readily understand how to determine the sequence similarity and identity of two polypeptides or nucleic acids. For example, the sequence similarity can be calculated after aligning the two sequences so that the identity is at its highest level. Alignments are dependent to some extent upon the use of the specific algorithm in alignment programs. This could include, for example, the local homology algorithm of Smith and Waterman *Adv. Appl. Math.* 2: 482 (1981), the homology alignment algorithm of Needleman and Wunsch, *J. MoL Biol.* 48: 443 (1970), the search for similarity method of Pearson and Lipman, *PNAS USA* 85: 2444 (1988), computerized implementations of these algorithms (GAP, BESTFIT, FASTA, and TFASTA in the Wisconsin Genetics Software Package, Genetics Computer Group, 575 Science Dr., Madison, Wis.), and the BLAST and BLAST 2.0 and algorithms described by Altschul et al., *Nucleic Acids Res.* 25:3389-3402, 1977; Altschul, et al., *J. Mol. Biol.* 215:403-410, 1990; Zuker, M. *Science* 244:48-52, 1989; Jaeger et al. *PNAS USA* 86:7706-7710, 1989 and Jaeger et al. *Methods Enzymol.* 183: 281-306, 1989. A recent review of multiple sequence alignment methods is provided by Nuin et al., BMC Bioinformatics 7:471, 2006. Each of these references is incorporated by reference at least for the material related to alignment and calculation of sequence similarity. It is understood that any of the methods of determining sequence similarity or identity typically can be used and that in certain instances the results of these various methods may differ. Where sequence similarity is provided as, for example, 95%, then such similarity must be detectable with at least one of the accepted methods of calculation.

The immunogenic polypeptides described herein can include one or more amino acid analogs or non-naturally occurring stereoisomers. These amino acid analogs and stereoisomers can readily be incorporated into polypeptide chains by charging tRNA molecules with the amino acid of choice and engineering genetic constructs that utilize, for example, amber codons, to insert the analog amino acid into a peptide chain in a site specific way (Thorson et al., *Methods in Molec. Biol.* 77:43-73 (1991), Zoller, *Current Opinion in Biotechnology,* 3:348-354 (1992); Ibba, *Biotechnology & Genetic Engineering Reviews* 13:197-216 (1995), Cahill et al., *TIBS,* 14(10):400-403 (1989); Benner, TIB Tech, 12:158-163 (1994); Ibba and Hennecke, *Biol technology,* 12:678-682 (1994) all of which are herein incorporated by reference at least for material related to amino acid analogs). Immunogenic fragments can be produced that resemble peptides, but which are not connected via a natural peptide linkage. For example, linkages for amino acids or amino acid analogs can include $-CH_2NH-$, $-CH_2S-$, $-CH_2-CH_2-$, $-CH=CH-$ (cis and trans), $-COCH_2-$, $-CH(OH)CH_2-$, and $-CHH_2SO-$ (These and others can be found in Spatola, A. F. "Peptide backbone modifications: A structure-activity analysis of peptides containing amide bond surrogates, conformational constraints, and related backbone modifications." In *Chemistry and Biochemistry of Amino Acids, Peptides, and Proteins*, pp. 267-357. Weinstein, B. editor, Marcel Dekker, New York, N.Y. (1983); Morley, *Trends in Pharm. Sci.* 1(2):463-468 (1980); Hudson, et al., *Int J Pept Prot Res* 14:177-185 (1979) ($-CH_2NH-$, $CH_2CH_2-$); Spatola et al. *Life Sci* 38:1243-1249 (1986) ($-CH H_2-S$); Hann, *Journal of the Chemical Society: Perkin Transactioins* 1 pp.307-314 (1982) ($-CH-CH-$, cis and trans); Almquist et al., *J. Med. Chem.* 23:1392-1398 (1980) ($-COCH_2-$); Jennings-White et al., *Tetrahedron Lett* 23:2533 (1982) ($-COCH_2-$); European Publication No. EP0045665 to Szelke, et al. (1982) ($-CH(OH)CH_2-$); Holladay et al., *Tetrahedron. Lett* 24:4401-3404 (1983) ($-C(OH)CH_2-$); and Hruby *Life Sci* 31:189-199 (1982) ($-CH_2-S-$); each of which is incorporated herein by reference at least for the material regarding linkages).

Amino acid analogs and stereoisomers often have enhanced or desirable properties, such as, more economical production, greater chemical stability, enhanced pharmacological properties (half-life, absorption, potency, efficacy, etc.), altered specificity (e.g., a broad-spectrum of biological activities), and others. For example, D-amino acids can be used to generate more stable peptides, because D-amino acids are not recognized by naturally occurring peptidases. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch *Ann. Rev. Biochem.* 61:387 (1992), incorporated herein by reference).

Other variants include those in which one or more immune targeting sequences (i.e., GYGRKKRRQRRR (TAT; SEQ ID NO.:19), RQIKIWFQNRRMKWKK (AntP; SEQ ID NO.: 20), SRRHHCRSKAKRSRHH (PER1-1; SEQ ID NO.:21), or GRRHHRRSKAKRSR (PER1-2; SEQ ID NO.:22)) is linked to the immunogenic PhtD polypeptide. Immunogenic fusion proteins may thus be produced and utilized in practicing the present invention.

In one embodiment, nucleic acids encoding a PhtD polypeptide such as any of SEQ ID NOS. 2, 3, or 4 or variants thereof are provided (i.e., SEQ ID NOS.: 5-10). Also provided are variants of such sequences, including degenerate variants thereof. In certain embodiments, a nucleic acid molecule encoding the peptide sequences may be inserted into expression vectors, as discussed below in greater detail. In such embodiments, the peptide sequences are encoded by nucleotides corresponding to the amino acid sequence. The particular combinations of nucleotides that encode the various amino acids are well known in the art, as described in various references used by those skilled in the art (e.g., Lewin, B. Genes V, Oxford University Press, 1994), as shown in Table 2 below. Nucleic acid variants may use any combination of nucleotides that encode the polypeptide of interest.

TABLE 2

| Phe | TTT | Ser | TCT | Tyr | TAT | Cys | TGT |
|---|---|---|---|---|---|---|---|
|  | TTC |  | TCC |  | TAC |  | TGC |
| Leu | TTA |  | TCA | TERM | TAA | TERM | TGA |
|  | TTG |  | TCG |  | TAG | Trp | TGG |
|  | CTT | Pro | CCT | His | CAT | Arg | CGT |
|  | CTC |  | CCC |  | CAC |  | CGC |
|  | CTA |  | CCA | Gln | CAA |  | CGA |
|  | CTG |  | CCG |  | CAG |  | CGG |
| Ile | ATT | Thr | ACT | Asn | AAT | Ser | AGT |
|  | ATC |  | ACC |  | AAC |  | AGC |
|  | ATA |  | ACA | Lys | AAA | Arg | AGA |
| Met | ATG |  | ACG |  | AAG |  | AGG |

TABLE 2-continued

| Val | GTT | Ala | GCT | Asp | GAT | Gly | GGT |
|---|---|---|---|---|---|---|---|
|  | GTC |  | GCC |  | GAC |  | GGC |
|  | GTA |  | GCA | Glu | GAA |  | GGA |
|  | GTG |  | GCG |  | GAG |  | GGG |

Exemplary nucleic acids encoding the polypeptides of SEQ ID NOS. 2, 3, 4, 15, 16 and 17, (i.e., with and without a His tag) are shown below:

Truncation 1 (without His tag)
(SEQ ID No: 5)
ATGTGGGTGCCCGACAGCAGACCCGAGCAGCCCAGCCCCCAGAGCACCCC

CGAGCCCAGCCCCAGCCCCAGCCCGCCCCCAACCCCCAGCCCGCCCCCA

GCAACCCCATCGACGAGAAGCTGGTGAAGGAGGCCGTGAGAAAGGTGGGC

GACGGCTACGTGTTCGAGGAGAACGGCGTGAGCAGATACATCCCCGCCAA

GGACCTGAGCGCCGAGACCGCCGCCGGCATCGACAGCAAGCTGGCCAAGC

AGGAGAGCCTGAGCCACAAGCTGGGCGCCAAGAAGACCGACCTGCCCAGC

AGCGACAGAGAGTTCTACAACAAGGCCTACGACCTGCTGGCCAGAATCCA

CCAGGACCTGCTGGACAACAAGGGCAGACAGGTGGACTTCGAGGCCCTGG

ACAACCTGCTGGAGAGACTGAAGGACGTGCCCAGCGACAAGGTGAAGCTG

GTGGACGACATCCTGGCCTTCCTGGCCCCCATCAGACACCCCGAGAGACT

GGGCAAGCCCAACGCCCAGATCACCTACACCGACGACGAGATCCAGGTGG

CCAAGCTGGCCGGCAAGTACACCACCGAGGACGGCTACATCTTCGACCCC

AGAGACATCACCAGCGACGAGGGCGACGCCTACGTGACCCCCCACATGAC

CCACAGCCACTGGATCAAGAAGGACAGCCTGAGCGAGGCCGAGAGAGCCG

CCGCCCAGGCCTACGCCAAGGAGAAGGGCCTGACCCCCCCCAGCACCGAC

CACCAGGACAGCGGCAACACCGAGGCCAAGGGCGCCGAGGCCATCTACAA

CAGAGTGAAGGCCGCCAAGAAGGTGCCCCTGGACAGAATGCCCTACAACC

TGCAGTACACCGTGGAGGTGAAGAACGGCAGCCTGATCATCCCCCACTAC

GACCACTACCACAACATCAAGTTCGAGTGGTTCGACGAGGGCCTGTACGA

GGCCCCCAAGGGCTACACCCTGGAGGACCTGCTGGCCACCGTGAAGTACT

ACGTGGAGCACCCCAACGAGAGACCCCACAGCGACAACGGCTTCGGCAAC

GCCAGCGACCACGTGAGAAAGAACAAGGTGGACCAGGACAGCAAGCCCGA

CGAGGACAAGGAGCACGACGAGGTGAGCGAGCCCACCCACCCCGAGAGCG

ACGAGAAGGAGAACCACGCCGGCCTGAACCCCAGCGCCGACAACCTGTAC

AAGCCCAGCACCGACACCGAGGAGACCGAGGAGGAGGCCGAGGACACCAC

CGACGAGGCCGAGATCCCCCAGGTGGAGAACAGCGTGATCAACGCCAAGA

TCGCCGACGCCGAGGCCCTGCTGGAGAAGGTGACCGACCCCAGCATCAGA

CAGAACGCCATGGAGACCCTGACCGGCCTGAAGAGCAGCCTGCTGCTGGG

CACCAAGGACAACAACACCATCAGCGCCGAGGTGGACAGCCTGCTGGCCC

TGCTGAAGGAGAGCCAGCCCGCCCCCATCCAG

Truncation 1 (His-tagged):
(SEQ ID No: 6)
ATGGGCCACCACCACCACCACCACTGGGTGCCCGACAGCAGACCCGAGCA

GCCCAGCCCCCAGAGCACCCCCGAGCCCAGCCCCAGCCCCCAGCCCGCCC

CCAACCCCCAGCCCGCCCCCAGCAACCCCATCGACGAGAAGCTGGTGAAG

GAGGCCGTGAGAAAGGTGGGCGACGGCTACGTGTTCGAGGAGAACGGCGT

GAGCAGATACATCCCCGCCAAGGACCTGAGCGCCGAGACCGCCGCCGGCA

TCGACAGCAAGCTGGCCAAGCAGGAGAGCCTGAGCCACAAGCTGGGCGCC

AAGAAGACCGACCTGCCCAGCAGCGACAGAGAGTTCTACAACAAGGCCTA

CGACCTGCTGGCCAGAATCCACCAGGACCTGCTGGACAACAAGGGCAGAC

AGGTGGACTTCGAGGCCCTGGACAACCTGCTGGAGAGACTGAAGGACGTG

CCCAGCGACAAGGTGAAGCTGGTGGACGACATCCTGGCCTTCCTGGCCCC

CATCAGACACCCCGAGAGACTGGGCAAGCCCAACGCCCAGATCACCTACA

CCGACGACGAGATCCAGGTGGCCAAGCTGGCCGGCAAGTACACCACCGAG

GACGGCTACATCTTCGACCCCAGAGACATCACCAGCGACGAGGGCGACGC

CTACGTGACCCCCCACATGACCCACAGCCACTGGATCAAGAAGGACAGCC

TGAGCGAGGCCGAGAGAGCCGCCGCCCAGGCCTACGCCAAGGAGAAGGGC

CTGACCCCCCCCAGCACCGACCACCAGGACAGCGGCAACACCGAGGCCAA

GGGCGCCGAGGCCATCTACAACAGAGTGAAGGCCGCCAAGAAGGTGCCCC

TGGACAGAATGCCCTACAACCTGCAGTACACCGTGGAGGTGAAGAACGGC

AGCCTGATCATCCCCCACTACGACCACTACCACAACATCAAGTTCGAGTG

GTTCGACGAGGGCCTGTACGAGGCCCCCAAGGGCTACACCCTGGAGGACC

TGCTGGCCACCGTGAAGTACTACGTGGAGCACCCCAACGAGAGACCCCAC

AGCGACAACGGCTTCGGCAACGCCAGCGACCACGTGAGAAAGAACAAGGT

GGACCAGGACAGCAAGCCCGACGAGGACAAGGAGCACGACGAGGTGAGCG

AGCCCACCCACCCCGAGAGCGACGAGAAGGAGAACCACGCCGGCCTGAAC

CCCAGCGCCGACAACCTGTACAAGCCCAGCACCGACACCGAGGAGACCGA

GGAGGAGGCCGAGGACACCACCGACGAGGCCGAGATCCCCCAGGTGGAGA

ACAGCGTGATCAACGCCAAGATCGCCGACGCCGAGGCCCTGCTGGAGAAG

GTGACCGACCCCAGCATCAGACAGAACGCCATGGAGACCCTGACCGGCCT

GAAGAGCAGCCTGCTGCTGGGCACCAAGGACAACAACACCATCAGCGCCG

AGGTGGACAGCCTGCTGGCCCTGCTGAAGGAGAGCCAGCCCGCCCCCATC

CAG

Truncation 2 (without His tag)
(SEQ ID No: 7)
ATGGTGAAGTACTACGTGGAGCACCCCAACGAGAGACCCCACAGCGACAA

CGGCTTCGGCAACGCCAGCGACCACGTGAGAAAGAACAAGGTGGACCAGG

ACAGCAAGCCCGACGAGGACAAGGAGCACGACGAGGTGAGCGAGCCCACC

CACCCCGAGAGCGACGAGAAGGAGAACCACGCCGGCCTGAACCCCAGCGC

CGACAACCTGTACAAGCCCAGCACCGACACCGAGGAGACCGAGGAGGAGG

CCGAGGACACCACCGACGAGGCCGAGATCCCCCAGGTGGAGAACAGCGTG

ATCAACGCCAAGATCGCCGACGCCGAGGCCCTGCTGGAGAAGGTGACCGA

CCCCAGCATCAGACAGAACGCCATGGAGACCCTGACCGGCCTGAAGAGCA

GCCTGCTGCTGGGCACCAAGGACAACAACACCATCAGCGCCGAGGTGGAC

AGCCTGCTGGCCCTGCTGAAGGAGAGCCAGCCCGCCCCCATCCAG

-continued

Truncation 2 (His-tagged):
(SEQ ID NO. 8)
ATGGGCCACCACCACCACCACCACGTGAAGTACTACGTGGAGCACCCCAA

CGAGAGACCCCACAGCGACAACGGCTTCGGCAACGCCAGCGACCACGTGA

GAAAGAACAAGGTGGACCAGGACAGCAAGCCCGACGAGGACAAGGAGCAC

GACGAGGTGAGCGAGCCCACCCACCCCGAGAGCGACGAGAAGGAGAACCA

CGCCGGCCTGAACCCCAGCGCCGACAACCTGTACAAGCCCAGCACCGACA

CCGAGGAGACCGAGGAGGAGGCCGAGGACACCACCGACGAGGCCGAGATC

CCCCAGGTGGAGAACAGCGTGATCAACGCCAAGATCGCCGACGCCGAGGC

CCTGCTGGAGAAGGTGACCGACCCCAGCATCAGACAGAACGCCATGGAGA

CCCTGACCGGCCTGAAGAGCAGCCTGCTGCTGGGCACCAAGGACAACAAC

ACCATCAGCGCCGAGGTGGACAGCCTGCTGGCCCTGCTGAAGGAGAGCCA

GCCCGCCCCCATCCAG

Truncation 3 (without His tag)
(SEQ ID NO. 9)
ATGCACGTGAGAAAGAACAAGGTGGACCAGGACAGCAAGCCCGACGAGGA

CAAGGAGCACGACGAGGTGAGCGAGCCCACCCACCCCGAGAGCGACGAGA

AGGAGAACCACGCCGGCCTGAACCCCAGCGCCGACAACCTGTACAAGCCC

AGCACCGACACCGAGGAGACCGAGGAGGAGGCCGAGGACACCACCGACGA

GGCCGAGATCCCCCAGGTGGAGAACAGCGTGATCAACGCCAAGATCGCCG

ACGCCGAGGCCCTGCTGGAGAAGGTGACCGACCCCAGCATCAGACAGAAC

GCCATGGAGACCCTGACCGGCCTGAAGAGCAGCCTGCTGCTGGGCACCAA

GGACAACAACACCATCAGCGCCGAGGTGGACAGCCTGCTGGCCCTGCTGA

AGGAGAGCCAGCCCGCCCCCATCCAG

Truncation 3 (His-tagged)
(SEQ ID NO. 10)
ATGGGCCACCACCACCACCACCACCACGTGAGAAAGAACAAGGTGGACCA

GGACAGCAAGCCCGACGAGGACAAGGAGCACGACGAGGTGAGCGAGCCCA

CCCACCCCGAGAGCGACGAGAAGGAGAACCACGCCGGCCTGAACCCCAGC

GCCGACAACCTGTACAAGCCCAGCACCGACACCGAGGAGACCGAGGAGGA

GGCCGAGGACACCACCGACGAGGCCGAGATCCCCCAGGTGGAGAACAGCG

TGATCAACGCCAAGATCGCCGACGCCGAGGCCCTGCTGGAGAAGGTGACC

GACCCCAGCATCAGACAGAACGCCATGGAGACCCTGACCGGCCTGAAGAG

CAGCCTGCTGCTGGGCACCAAGGACAACAACACCATCAGCGCCGAGGTGG

ACAGCCTGCTGGCCCTGCTGAAGGAGAGCCAGCCCGCCCCCATCCAG

Also provided are isolated nucleic acids that hybridize under highly stringent conditions to any portion of a hybridization probe corresponding to a nucleotide sequence encoding any of SEQ ID NOS. 2, 3, 4, 15, 16, and/or 17 or to any of SEQ ID NOS. 5-10. The hybridizing portion of the hybridizing nucleic acid is typically at least 15 (e.g., 15, 20, 25, 30, 40, or more) nucleotides in length. The hybridizing portion is at least 65%, 80%, 90%, 95%, or 99% identical to a portion of the sequence to which it hybridizes. Hybridizing nucleic acids are useful, for example, as cloning probes, primers (e.g., PCR primer), or diagnostic probes. Nucleic acid duplex or hybrid stability is expressed as the melting temperature or Tm, which is the temperature at which a probe dissociates from a target DNA. This melting temperature is used to define the required stringency conditions. If sequences are identified that are related and substantially identical to the probe, rather than identical, then it is useful to first establish the lowest temperature at which only homologous hybridization occurs with a particular concentration of salt (e.g. using various concentrations of SSC or SSPE buffers). Assuming that a 1% mismatching results in a 1° C. decrease in Tm, the temperature of the final wash in the hybridization reaction is reduced accordingly (for example, if sequences having more than 95% identity are sought, the final wash temperature is decreased by 5° C.). In practice, the change in Tm can be between 0.5 and 1.5° C. per 1% mismatch. Highly stringent conditions involve hybridizing at 68° C. in 5× SSC/5× Denhardt's solution/1.0% SDS, and washing in 0.2× SSC/0.1% SDS at room temperature. "Moderately stringent conditions" include washing in 3× SSC at 42° C. Salt concentrations and temperatures can be varied to achieve the optimal level of identity between the probe and the target nucleic acid. Additional guidance regarding such stringency conditions is readily available in the art, for example, in *Molecular Cloning: A Laboratory Manual, Third Edition* by Sambrook et al., Cold Spring Harbor Press, 2001.

Expression vectors may also be suitable for use in practicing the present invention. Expression vectors are typically comprised of a flanking sequence operably linked to a heterologous nucleic acid sequence encoding a polypeptide (the "coding sequence"). In other embodiments, or in combination with such embodiments, a flanking sequence is preferably capable of effecting the replication, transcription and/or translation of the coding sequence and is operably linked to a coding sequence. To be "operably linked" indicates that the nucleic acid sequences are configured so as to perform their usual function. For example, a promoter is operably linked to a coding sequence when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered operably linked to the coding sequence. Flanking sequences may be homologous (i.e., from the same species and/or strain as the host cell), heterologous (i.e., from a species other than the host cell species or strain), hybrid (i.e., a combination of flanking sequences from more than one source), or synthetic. A flanking sequence may also be a sequence that normally functions to regulate expression of the nucleotide sequence encoding the polypeptide in the genome of the host.

In certain embodiments, it is preferred that the flanking sequence is a transcriptional regulatory region that drives high-level gene expression in the target cell. The transcriptional regulatory region may comprise, for example, a promoter, enhancer, silencer, repressor element, or combinations thereof. The transcriptional regulatory region may be either constitutive or tissue- or cell-type specific (i.e., the region drives higher levels of transcription in one type of tissue or cell as compared to another). As such, the source of a transcriptional regulatory region may be any prokaryotic or eukaryotic organism, any vertebrate or invertebrate organism, or any plant, provided that the flanking sequence is functional in, and can be activated by, the host cell machinery. A wide variety of transcriptional regulatory regions may be utilized in practicing the present invention.

Suitable transcriptional regulatory regions include, among others, the CMV promoter (i.e., the CMV-immediate early promoter); promoters from eukaryotic genes (i.e., the estrogen-inducible chicken ovalbumin gene, the interferon genes, the gluco-corticoid-inducible tyrosine aminotransferase gene, and the thymidine kinase gene); the major early and late adenovirus gene promoters; the SV40 early promoter region (Bernoist and Chambon, 1981, *Nature* 290:304-10); the promoter contained in the 3' long terminal repeat (LTR) of Rous sarcoma virus (RSV) (Yamamoto, et al., 1980, *Cell* 22:787-97); the herpes simplex virus thymidine kinase (HSV-TK) promoter (Wagner et al., 1981, *Proc. Natl. Acad. Sci. U.S.A.* 78:1444-45); the regulatory sequences of the metallothionine gene (Brinster et al., 1982, *Nature* 296:39-42); or in the regulatory sequences found in prokaryotic expression vectors such as the beta-lactamase promoter (Villa-Kamaroff et al., 1978, *Proc. Natl. Acad. Sci. U.S.A.*, 75:3727-31), the tac promoter (DeBoer et al., 1983, Proc. Natl. Acad. Sci. U.S.A., 80:21-25), or those in the T7 RNA polymerase promoter, the pBAD arabinose promoter, or the pTrc promoter. Tissue- and/or cell-type specific transcriptional control regions include, for example, the elastase I gene control region which is active in pancreatic acinar cells (Swift et al., 1984, *Cell* 38:639-46; Ornitz et al., 1986, *Cold Spring Harbor Symp. Quant. Biol.* 50:399-409 (1986); MacDonald, 1987, *Hepatology* 7:425-515); the insulin gene control region which is active in pancreatic beta cells (Hanahan, 1985, *Nature* 315:115-22); the immunoglobulin gene control region which is active in lymphoid cells (Grosschedl et al., 1984, *Cell* 38:647-58; Adames et al., 1985, *Nature* 318:533-38; Alexander et al., 1987, *Mol. Cell. Biol.*, 7:1436-44); the mouse mammary tumor virus control region in testicular, breast, lymphoid and mast cells (Leder et al., 1986, *Cell* 45:485-95); the albumin gene control region in liver (Pinkert et al., 1987, *Genes and Devel.* 1:268-76); the alpha-feto-protein gene control region in liver (Krumlauf et al., 1985, *Mol. Cell. Biol.*, 5:1639-48; Hammer et al., 1987, *Science* 235:53-58); the alpha 1-antitrypsin gene control region in liver (Kelsey et al., 1987, *Genes and Devel.* 1:161-71); the beta-globin gene control region in myeloid cells (Mogram et al., 1985, *Nature* 315:338-40; Kollias et al., 1986, *Cell* 46:89-94); the myelin basic protein gene control region in oligodendrocyte cells in the brain (Readhead et al., 1987, *Cell* 48:703-12); the myosin light chain-2 gene control region in skeletal muscle (Sani, 1985, *Nature* 314: 283-86); and the gonadotropic releasing hormone gene control region in the hypothalamus (Mason et al., 1986, *Science* 234:1372-78), and the tyrosinase promoter in melanoma cells (Hart, I. Semin Oncol 1996 February;23(1):154-8; Siders, et al. Cancer Gene Ther 1998 September-October;5(5):281-91). Other suitable promoters are known in the art.

The nucleic acid molecule encoding the targeted immunogen may be administered as part of a viral or a non-viral vector. In one embodiment, a DNA vector is utilized to deliver nucleic acids encoding the targeted immunogen and/or associated molecules (e.g., co-stimulatory molecules, cytokines or chemokines) to the patient. In doing so, various strategies may be utilized to improve the efficiency of such mechanisms including, for example, the use of self-replicating viral replicons (Caley, et al. 1999. *Vaccine,* 17: 3124-2135; Dubensky, et al. 2000. *Mol. Med.* 6: 723-732; Leitner, et al. 2000. *Cancer Res.* 60: 51-55), codon optimization (Liu, et al. 2000. *Mol. Ther.,* 1: 497-500; Dubensky, supra; Huang, et al. 2001. *J. Virol.* 75: 4947-4951), in vivo electroporation (Widera, et al. 2000. *J. Immunol.* 164: 4635-3640), incorporation of nucleic acids encoding co-stimulatory molecules, cytokines and/or chemokines (Xiang, et al. 1995. *Immunity,* 2: 129-135; Kim, et al. 1998. *Eur. J. Immunol.,* 28: 1089-1103; Iwasaki, et al. 1997. *J. Immunol.* 158: 4591-3601; Sheerlinck, et al. 2001. *Vaccine,* 19: 2647-2656), incorporation of stimulatory motifs such as CpG (Gurunathan, supra; Leitner, supra), sequences for targeting of the endocytic or ubiquitin-processing pathways (Thomson, et al. 1998. *J. Virol.* 72: 2246-2252; Velders, et al. 2001. *J. Immunol.* 166: 5366-5373), prime-boost regimens (Gurunathan, supra; Sullivan, et al. 2000. *Nature,* 408: 605-609; Hanke, et al. 1998. Vaccine, 16: 439-445; Amara, et al. 2001. *Science,* 292: 69-74), proteasome-sensitive cleavage sites, and the use of mucosal delivery vectors such as *Salmonella* (Darji, et al. 1997. *Cell,* 91: 765-775; Woo, et al. 2001. Vaccine, 19: 2945-2954). Other methods are known in the art, some of which are described below.

Various viral vectors that have been successfully utilized for introducing a nucleic acid to a host include retrovirus, adenovirus, adeno-associated virus (AAV), herpes virus, and poxvirus, among others. It is understood in the art that many such viral vectors are available in the art. The vectors of the present invention may be constructed using standard recombinant techniques widely available to one skilled in the art. Such techniques may be found in common molecular biology references such as *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), and PCR Protocols: A Guide to Methods and Applications (Innis, et al. 1990. Academic Press, San Diego, Calif.).

Preferred retroviral vectors are derivatives of lentivirus as well as derivatives of murine or avian retroviruses. Examples of suitable retroviral vectors include, for example, Moloney murine leukemia virus (MoMuLV), Harvey murine sarcoma virus (HaMuSV), murine mammary tumor virus (MuMTV), SIV, BIV, HIV and Rous Sarcoma Virus (RSV). A number of retroviral vectors can incorporate multiple exogenous nucleic acid sequences. As recombinant retroviruses are defective, they require assistance in order to produce infectious vector particles. This assistance can be provided by, for example, helper cell lines encoding retrovirus structural genes. Suitable helper cell lines include Ψ2, PA317 and PA12, among others. The vector virions produced using such cell lines may then be used to infect a tissue cell line, such as NIH 3T3 cells, to produce large quantities of chimeric retroviral virions. Retroviral vectors may be administered by traditional methods (e.g., injection) or by implantation of a "producer cell line" in proximity to the target cell population (Culver, K., et al., 1994, *Hum. Gene Ther.,* 5 (3): 343-79; Culver, K., et al., i Cold Spring Harb. Symp. Quant. Biol., 59: 685-90); Oldfield, E., 1993, *Hum. Gene Ther.,* 4 (1): 39-69). The producer cell line is engineered to produce a viral vector and releases viral particles in the vicinity of the target cell. A portion of the released viral particles contact the target cells and infect those cells, thus delivering a nucleic acid of the present invention to the target cell. Following infection of the target cell, expression of the nucleic acid of the vector occurs.

Adenoviral vectors have proven especially useful for gene transfer into eukaryotic cells (Rosenfeld, M., et al., 1991, *Science,* 252 (5004): 431-3; Crystal, R., et al., 1994, *Nat. Genet.,* 8 (1): 42-51), the study of eukaryotic gene expression (Levrero, M., et al., 1991, *Gene,* 101 (2): 195-202), vaccine development (Graham, F. and Prevec, L., 1992, *Biotechnology,* 20: 363-90), and in animal models (Stratford-Perricaudet, L., et al., 1992, *Bone Marrow Transplant.,* 9 (Suppl. 1): 151-2; Rich, D., et al., 1993, *Hum. Gene Ther.,* 4 (4): 461-76). Experimental routes for administering recombinant Ad to different tissues in vivo have included intratracheal instillation (Rosenfeld, M., et al., 1992, *Cell,* 68 (1): 143-55) injection into muscle (Quantin, B., et al., 1992, *Proc. Natl. Acad. Sci. U.S.A.,* 89 (7): 2581-3), peripheral intravenous injection (Herz, J., and Gerard, R., 1993, *Proc. Natl. Acad. Sci. U.S.A.,*

90 (7): 2812-6) and stereotactic inoculation to brain (Le Gal La Salle, G., et al., 1993, *Science,* 259 (5097): 988-90), among others.

Adeno-associated virus (AAV) demonstrates high-level infectivity, broad host range and specificity in integrating into the host cell genome (Hermonat, P., et al., 1984, *Proc. Natl. Acad. Sci. U.S.A.,* 81 (20): 6466-70). And Herpes Simplex Virus type-1 (HSV-1) is yet another attractive vector system, especially for use in the nervous system because of its neurotropic property (Geller, A., et al., 1991, *Trends Neurosci.,* 14 (10): 428-32; Glorioso, et al., 1995, *Mol. Biotechnol.,* 4 (1): 87-99; Glorioso, et al., 1995, *Annu. Rev. Microbiol.,* 49: 675-710).

Poxvirus is another useful expression vector (Smith, et al. 1983, *Gene,* 25 (1): 21-8; Moss, et al, 1992, *Biotechnology,* 20: 345-62; Moss, et al, 1992, *Curr. Top. Microbiol. Immunol.,* 158: 25-38; Moss, et al. 1991. *Science,* 252: 1662-1667). Poxviruses shown to be useful include vaccinia, NYVAC, avipox, fowlpox, canarypox, ALVAC, and ALVAC(2), among others.

NYVAC (vP866) was derived from the Copenhagen vaccine strain of vaccinia virus by deleting six nonessential regions of the genome encoding known or potential virulence factors (see, for example, U.S. Pat. Nos. 5,364,773 and 5,494, 807). The deletion loci were also engineered as recipient loci for the insertion of foreign genes. The deleted regions are: thymidine kinase gene (TK; J2R) vP410; hemorrhagic region (u; B13R+B14R) vP553; A type inclusion body region (ATI; A26L) vP618; hemagglutinin gene (HA; A56R) vP723; host range gene region (C7L-K1L) vP804; and, large subunit, ribonucleotide reductase (I4L) vP866. NYVAC is a genetically engineered vaccinia virus strain that was generated by the specific deletion of eighteen open reading frames encoding gene products associated with virulence and host range. NYVAC has been show to be useful for expressing TAs (see, for example, U.S. Pat. No. 6,265,189). NYVAC (vP866), vP994, vCP205, vCP1433, placZH6H4Lreverse, pMPC6H6K3E3 and pC3H6FHVB were also deposited with the ATCC under the terms of the Budapest Treaty, accession numbers VR-2559, VR-2558, VR-2557, VR-2556, ATCC-97913, ATCC-97912, and ATCC-97914, respectively.

ALVAC-based recombinant viruses (i.e., ALVAC-1 and ALVAC-2) are also suitable for use in practicing the present invention (see, for example, U.S. Pat. No. 5,756,103). ALVAC(2) is identical to ALVAC(1) except that ALVAC(2) genome comprises the vaccinia E3L and K3L genes under the control of vaccinia promoters (U.S. Pat. No. 6,130,066; Beattie et al., 1995a, 1995b, 1991; Chang et al., 1992; Davies et al., 1993). Both ALVAC(1) and ALVAC(2) have been demonstrated to be useful in expressing foreign DNA sequences, such as TAs (Tartaglia et al., 1993 a,b; U.S. Pat. No. 5,833, 975). ALVAC was deposited under the terms of the Budapest Treaty with the American Type Culture Collection (ATCC), 10801 University Boulevard, Manassas, Va. 20110-2209, USA, ATCC accession number VR-2547.

Another useful poxvirus vector is TROVAC. TROVAC refers to an attenuated fowlpox that was a plaque-cloned isolate derived from the FP-1 vaccine strain of fowlpoxvirus which is licensed for vaccination of 1 day old chicks. TROVAC was likewise deposited under the terms of the Budapest Treaty with the ATCC, accession number 2553.

"Non-viral" plasmid vectors may also be suitable in certain embodiments. Preferred plasmid vectors are compatible with bacterial, insect, and/or mammalian host cells. Such vectors include, for example, PCR-II, pCR3, and pcDNA3.1 (Invitrogen, San Diego, Calif.), pBSII (Stratagene, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII, Invitrogen), pDSR-alpha (PCT pub. No. WO 90/14363) and pFastBacDual (Gibco-BRL, Grand Island, N.Y.) as well as Bluescript® plasmid derivatives (a high copy number COLE1-based phagemid, Stratagene Cloning Systems, La Jolla, Calif.), PCR cloning plasmids designed for cloning Taq-amplified PCR products (e.g., TOPO™ TA cloning® kit, PCR2.1® plasmid derivatives, Invitrogen, Carlsbad, Calif.). Bacterial vectors may also be used with the current invention. These vectors include, for example, *Shigella, Salmonella, Vibrio cholerae, Lactobacillus, Bacille calmette guerin* (BCG), and *Streptococcus* (see for example, WO 88/6626; WO 90/0594; WO 91/13157; WO 92/1796; and WO 92/21376). Many other non-viral plasmid expression vectors and systems are known in the art and could be used with the current invention.

Other delivery techniques may also suffice in practicing the present invention including, for example, DNA-ligand complexes, adenovirus-ligand-DNA complexes, direct injection of DNA, $CaPO_4$ precipitation, gene gun techniques, electroporation, and colloidal dispersion systems. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome, which are artificial membrane vesicles useful as delivery vehicles in vitro and in vivo. RNA, DNA and intact virions can be encapsulated within the aqueous interior and be delivered to cells in a biologically active form (Fraley, R., et al., 1981, *Trends Biochem. Sci.,* 6: 77). The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

A cultured cell comprising the vector is also provided. The cultured cell can be a cultured cell transfected with the vector or a progeny of the cell, wherein the cell expresses the immunogenic polypeptide. Suitable cell lines are known to those of skill in the art and are commercially available, for example, through the American Type Culture Collection (ATCC). The transfected cells can be used in a method of producing an immunogenic polypeptide. The method comprises culturing a cell comprising the vector under conditions that allow expression of the immunogenic polypeptide, optionally under the control of an expression sequence. The immunogenic polypeptide can be isolated from the cell or the culture medium using standard protein purification methods.

The immunogenic polypeptides can be made using standard enzymatic cleavage of larger polypeptides or proteins or can be generated by linking two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert -butyloxycarbonyl) chemistry (Applied Biosystems, Inc., Foster City, Calif.). By peptide condensation reactions, native chemical ligation, solid phase chemistry, or enzymatic ligation, two fragments can be covalently joined via a peptide bond at their carboxyl and amino termini to form an immunogenic PhtD polypeptide. (Synthetic Peptides: A User Guide., Grant, ed., W. H. Freeman and Co., New York, N.Y. (1992); Principles of Peptide Synthesis., Bodansky and Trost, eds. Springer-Verlag Inc., New York, N.Y. (1993); Abrahmsen L et al., *Biochemistry,* 30:4151 (1991); Dawson et al. *Science,* 266:776-779 (1994); *Solid Phase Peptide Synthesis,* $2^{nd}$ Edition, Stewart, ed., Pierce Chemical Company, Rockford, Ill., (1984), all of which are incorporated herein by reference for the methods described therein).

The immunogenic polypeptides and compositions comprising one or more polypeptides may be used to generate antibodies. Thus, a method of generating antibodies specific to PhtD in a subject comprises administering to the subject an immunogenic PhtD fragment described herein. Also provided herein are antibodies (or fragments or derivatives thereof) that bind the PhtD polypeptides.

Antibodies may be polyclonal or monoclonal, may be fully human or humanized, and include naturally occurring antibodies and single-chain antibodies. Antibodies can be made in vivo by administering to a subject an immunogenic PhtD polypeptide or fragment or derivative thereof. In vitro antibody production includes making monoclonal antibodies using hybridoma methods. Hybridoma methods are well known in the art and are described by Kohler and Milstein, *Nature,* 256:495 (1975) and Harlow and Lane. Antibodies, A Laboratory Manual. Cold Spring Harbor Publications, New York, (1988), which are incorporated by reference in their entirety for the methods described therein.

Methods for the production of single-chain antibodies are well known to those of skill in the art. See, for example, U.S. Pat. No. 5,359,046, (incorporated herein by reference in its entirety for such methods). A single chain antibody is created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation. See, for example, Huston, J. S., et al., *Methods in Enzym.* 203:46-121 (1991), which is incorporated herein by reference for its material regarding linkers.

Fully human and humanized antibodies to the PhtD polypeptides may be used in the methods described herein. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Transgenic animals (e.g., mice) that are capable, upon immunization, of producing a full repertoire of human antibodies (i.e., fully human antibodies) may be employed. The homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice results in the production of human antibodies upon antigen challenge (see, e.g., Jakobovits et al., *PNAS USA,* 90:2551-255 (1993); Jakobovits et al., *Nature,* 362:255-258 (1993); Bruggemann et al., *Year in Immuno.,* 7:33 (1993)). Human antibodies can also be produced in phage display libraries (Hoogenboom et al., *J. Mol. Biol.,* 227:381 (1991); Marks et al., *J. Mol. Biol.,* 222:581 (1991)). The techniques of Cote et al. and Boemer et al. also describe methods for the preparation of human monoclonal antibodies (Cole, et al., "The EBV-hybridoma technique and its application to human lung cancer." In, *Monoclonal Antibodies and Cancer Therapy,* Volume 27, Reisfeld and Sell, eds., pp. 77-96, Alan R. Liss, Inc., New York, N.Y., (1985); Boemer et al., *J. Immunol.,* 147(1):86-95 (1991)). These references are incorporated by reference in their entirety for the methods described therein.

Antibody fragment as used herein includes F(ab')2, Fab', and Fab fragments, including hybrid fragments. Such fragments of the antibodies retain the ability to bind a specific PhtD polypeptide. Methods can be used to construct (ab) expression libraries (see e.g., Huse, et al., 1989 *Science* 246: 1275-1281) to allow rapid and effective identification of monoclonal F(ab) fragments with the desired specificity for a PhtD polypeptide. Antibody fragments that contain the idiotypes to the polypeptide may be produced by techniques known in the art including, but not limited to: (i) an F(ab')2 fragment produced by pepsin digestion of an antibody molecule; (ii) an Fab fragment generated by reducing the disulfide bridges of an F(ab')2 fragment; (iii) an F(ab) fragment generated by the treatment of the antibody molecule with papain and a reducing agent and (iv) F(v) fragments.

A composition comprising an immunogenic polypeptide of PhtD and a pharmaceutically acceptable carrier are described herein. Optionally, the composition further comprises an adjuvant. Compositions comprising the immunogenic polypeptide may contain combinations of other immunogenic polypeptides, including, for example, an immunogenic Streptococcus polypeptide or immunogenic fragments of PspA, NanA, PsaA, pneumolysin, PspC, or any combination thereof.

Optionally, the compositions described herein are suitable for administration to a mucosal surface. The composition can be a nasal spray, a nebulizer solution, or an aerosol inhalant, for example. Thus the composition may be present in a container and the container may be a nasal sprayer, a nebulizer, or an inhaler.

By pharmaceutically acceptable carrier is meant a material that is not biologically or otherwise undesirable, i.e., the material may be administered to a subject, along with the immunogenic fragment of PhtD, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Suitable carriers and their formulations are described in *Remington: The Science and Practice of Pharmacy,* $21^{st}$ Edition, David B. Troy, ed., Lippicott Williams & Wilkins (2005). Typically, an appropriate amount of a pharmaceutically-acceptable salt is used in the formulation to render the formulation isotonic. Examples of the pharmaceutically-acceptable carriers include, but are not limited to, sterile water, saline, buffered solutions like Ringer's solution, and dextrose solution. The pH of the solution is generally from about 5 to about 8 or from about 7 to about 7.5. Other carriers include sustained release preparations such as semipermeable matrices of solid hydrophobic polymers containing the immunogenic PhtD polypeptides. Matrices are in the form of shaped articles, e.g., films, liposomes or microparticles. It will be apparent to those persons skilled in the art that certain carriers may be more preferable depending upon, for instance, the route of administration and concentration of composition being administered. Carriers are those suitable for administration of the PhtD immunogenic fragments to humans or other subjects.

Pharmaceutical compositions may include carriers, thickeners, diluents, buffers, preservatives, surface active agents, adjuvants, immunostimulants, in addition to the immunogenic polypeptide. Pharmaceutical compositions may also include one or more active ingredients such as antimicrobial agents, antiinflammatory agents and anesthetics. Adjuvants may also be included to stimulate or enhance the immune response against PhtD. Non-limiting examples of suitable classes of adjuvants include those of the gel-type (i.e., aluminum hydroxide/phosphate ("alum adjuvants"), calcium phosphate, microbial origin (muramyl dipeptide (MDP)), bacterial exotoxins (cholera toxin (CT), native cholera toxin subunit B (CTB), *E. coli* labile toxin (LT), pertussis toxin (PT), CpG oligonucleotides, BCG sequences, tetanus toxoid, monophosphoryl lipid A (MPL) of, for example, *E. coli*, Salmonella minnesota, Salmonella typhimurium, or Shigella exseri), particulate adjuvants (biodegradable, polymer microspheres), immunostimulatory complexes (ISCOMs)), oil-emulsion and surfactant-based adjuvants (Freund's incomplete adjuvant (FIA), microfluidized emulsions (MF59, SAF), saponins (QS-21)), synthetic (muramyl peptide derivatives (murabutide, threony-MDP), nonionic block copolymers (L121), polyphosphazene (PCCP), synthetic polynucleotides (poly A :U, poly I :C), thalidomide derivatives (CC-4407/ACTIMID)), RH3-ligand, or polylactide glycolide (PLGA) microspheres, among others. Fragments, homologs, derivatives, and fusions to any of these toxins are also suitable, provided that they retain adjuvant activity. Suitable mutants or variants of adjuvants are described, e.g., in WO 95/17211 (Arg-7-Lys CT mutant), WO 96/6627 (Arg-192-Gly LT mutant), and WO 95/34323 (Arg-9-Lys and Glu-129-Gly PT mutant). Additional LT mutants that can be used in the methods and compositions of the invention include, e. g., Ser-63-Lys, Ala-69-Gly, Glu-110-Asp, and Glu-112-Asp mutants.

Metallic salt adjuvants such as alum adjuvants are well-known in the art as providing a safe excipient with adjuvant activity. The mechanism of action of these adjuvants are thought to include the formation of an antigen depot such that antigen may stay at the site of injection for up to 3 weeks after administration, and also the formation of antigen/metallic salt complexes which are more easily taken up by antigen presenting cells. In addition to aluminium, other metallic salts have been used to adsorb antigens, including salts of zinc, calcium, cerium, chromium, iron, and berilium. The hydroxide and phosphate salts of aluminium are the most common. Formulations or compositions containing aluminium salts, antigen, and an additional immunostimulant are known in the art. An example of an immunostimulant is 3-de-O-acylated monophosphoryl lipid A (3D-MPL).

One or more cytokines may also be suitable co-stimulatory components in practicing the present invention, either as polypeptides or as encoded by nucleic acids contained within the compositions of the present invention (Parmiani, et al. Immunol Lett 2000 September 15; 74(1): 41-3; Berzofsky, et al. Nature Immunol. 1: 209-219). Suitable cytokines include, for example, interleukin-2 (IL-2) (Rosenberg, et al. *Nature Med.* 4: 321-327 (1998)), IL-4, IL-7, IL-12 (reviewed by Pardoll, 1992; Harries, et al. J. Gene Med. 2000 July-August; 2(4):243-9; Rao, et al. *J. Immunol.* 156: 3357-3365 (1996)), IL-15 (Xin, et al. Vaccine, 17:858-866, 1999), IL-16 (Cruikshank, et al. J. Leuk Biol. 67(6): 757-66, 2000), IL-18 (*J. Cancer Res. Clin. Oncol.* 2001. 127(12): 718-726), GM-CSF (CSF (Disis, et al. *Blood,* 88: 202-210 (1996)), tumor necrosis factor-alpha (TNF-$\alpha$), or interferon-gamma (INF-$\gamma$). Other cytokines may also be suitable for practicing the present invention, as is known in the art.

Chemokines may also be used to assist in inducing or enhancing the immune response. For example, fusion proteins comprising CXCL10 (IP-10) and CCL7 (MCP-3) fused to a tumor self-antigen have been shown to induce anti-tumor immunity (Biragyn, et al. *Nature Biotech.* 1999, 17: 253-258). The chemokines CCL3 (MIP-1$\alpha$) and CCL5 (RANTES) (Boyer, et al. *Vaccine,* 1999, 17 (Supp. 2): S53-S64) may also be of use in practicing the present invention. Other suitable chemokines are known in the art.

In certain embodiments, the targeted immunogen may be utilized as a nucleic acid molecule, either alone or as part of a delivery vehicle such as a viral vector. In such cases, it may be advantageous to combine the targeted immunogen with one or more co-stimulatory component(s) such as cell surface proteins, cytokines or chemokines in a composition of the present invention. The co-stimulatory component may be included in the composition as a polypeptide or as a nucleic acid encoding the polypeptide, for example. Suitable co-stimulatory molecules include, for instance, polypeptides that bind members of the CD28 family (i.e., CD28, ICOS; Hutloff, et al. *Nature* 1999, 397: 263-265; Peach, et al. *J Exp Med* 1994, 180: 2049-2058) such as the CD28 binding polypeptides B7.1 (CD80; Schwartz, 1992; Chen et al, 1992; Ellis, et al. *J. Immunol.,* 156(8): 2700-9) and B7.2 (CD86; Ellis, et al. *J. Immunol.,* 156(8): 2700-9); polypeptides which bind members of the integrin family (i.e., LFA-1 (CD11a/CD18); Sedwick, et al. *J Immunol* 1999, 162: 1367-1375; Wülfing, et al. *Science* 1998, 282: 2266-2269; Lub, et al. *Immunol Today* 1995, 16: 479-483) including members of the ICAM family (i.e., ICAM-1, -2 or -3); polypeptides which bind CD2 family members (i.e., CD2, signalling lymphocyte activation molecule (CDw150 or "SLAM"; Aversa, et al. *J Immunol* 1997, 158: 4036-4044) such as CD58 (LFA-3; CD2 ligand; Davis, et al. *Immunol Today* 1996, 17: 177-187) or SLAM ligands (Sayos, et al. *Nature* 1998, 395: 462-469); polypeptides which bind heat stable antigen (HSA or CD24; Zhou, et al. *Eur J Immunol* 1997, 27: 2524-2528); polypeptides which bind to members of the TNF receptor (TNFR) family (i.e., 4-1BB (CD137; Vinay, et al. *Semin Immunol* 1998, 10: 481-489), OX40 (CD134; Weinberg, et al. *Semin Immunol* 1998, 10: 471-480; Higgins, et al. *J Immunol* 1999, 162: 486-493), and CD27 (Lens, et al. *Semin Immunol* 1998, 10: 491-499)) such as 4-1BBL (4-1BB ligand; Vinay, et al. *Semin Immunol* 1998, 10: 481-48; DeBenedette, et al. *J Immunol* 1997, 158: 551-559), TNFR associated factor-1 (TRAF-1; 4-1BB ligand; Saoulli, et al. *J Exp Med* 1998, 187: 1849-1862, Arch, et al. *Mol Cell Biol* 1998, 18: 558-565), TRAF-2 (4-1BB and OX40 ligand; Saoulli, et al. JExp Med 1998, 187: 1849-1862; Oshima, et al. *Int Immunol* 1998, 10: 517-526, Kawamata, et al. *J Biol Chem* 1998, 273: 5808-5814), TRAF-3 (4-1BB and OX40 ligand; Arch, et al. *Mol Cell Biol* 1998, 18: 558-565; Jang, et al. *Biochem Biophys Res Commun* 1998, 242: 613-620; Kawamata S, et al. *J Biol Chem* 1998, 273: 5808-5814), OX40L (OX40 ligand; Gramaglia, et al. *J Immunol* 1998, 161: 6510-6517), TRAF-5 (OX40 ligand; Arch, et al. *Mol Cell Biol* 1998, 18: 558-565; Kawamata, et al. *J Biol Chem* 1998, 273: 5808-5814), and CD70 (CD27 ligand; Couderc, et al. *Cancer Gene Ther.,* 5(3): 163-75). CD154 (CD40 ligand or "CD40L"; Gurunathan, et al. *J.*

Immunol., 1998, 161: 4563-4571; Sine, et al. *Hum. Gene Ther.*, 2001, 12: 1091-1102) may also be suitable. Stimulatory motifs other than co-stimulatory molecules per se may be incorporated into nucleic acids encoding TAs, such as CpG motifs (Gurunathan, et al. *Ann. Rev. Immunol.*, 2000, 18: 927-974). These reagents and methods, as well as others known by those of skill in the art, may be utilized in practicing the present invention.

Other examples of substantially non-toxic, biologically active adjuvants of the present invention include hormones, enzymes, growth factors, or biologically active portions thereof. Such hormones, enzymes, growth factors, or biologically active portions thereof can be of human, bovine, porcine, ovine, canine, feline, equine, or avian origin, for example, and can be tumor necrosis factor (TNF), prolactin, epidermal growth factor (EGF), granulocyte colony stimulating factor (GCSF), insulin-like growth factor (IGF-1), somatotropin (growth hormone) or insulin, or any other hormone or growth factor whose receptor is expressed on cells of the immune system.

Provided are methods of making and using the immunogenic polypeptides described herein and compositions useful in such methods. The polypeptides can be generated using standard molecular biology techniques and expression systems. (See, for example, *Molecular Cloning: A Laboratory Manual, Third Edition* by Sambrook et al., Cold Spring Harbor Press, 2001). For example, a fragment of a gene that encodes an immunogenic polypeptide may be isolated and the polynucleotide encoding the immunogenic polypeptide may be cloned into any commercially available expression vector (such as pBR322 and pUC vectors (New England Biolabs, Inc., Ipswich, Mass.)) or expression/purification vectors (such as GST fusion vectors (Pfizer, Inc., Piscataway, N.J.)) and then expressed in a suitable procaryotic, viral or eucaryotic host. Purification may then be achieved by conventional means or, in the case of a commercial expression/purification system, in accordance with manufacturer's instructions.

Methods of detecting PhtD expression to differentiate pneumococcal pneumonia from other forms of pneumonia are provided. The major reservoir of pneumococci in the world resides in human nasal carriage. Acquisition of infection is generally from a carrier and infection is always preceded by nasal carriage. The colonization of the nasopharynx is considered a prerequisite for the spread of pneumococci to the lower respiratory tract, the nasal sinuses, and the middle ear.

To determine efficacy of pneumococcal vaccines it is necessary to know which subjects have pneumococcal pneumonia and which ones do not. The standard procedure for diagnosing pneumonia is by X-ray or other diagnostic and a positive blood culture for *Streptococcus pneumoniae*. Subjects satisfying these criteria are assumed to have pneumococcal pneumonia. Unfortunately this method misses between 75 and 85 percent of patients with pneumococcal pneumonia, because it has been estimated that only 15-25% of patients with pneumonia also have bacteremia (Fedson, et al., *Vaccine* 17:Suppl. 1:S11-18 (1999); Ostergaard and Andersen, *Chest* 104:1400-1407 (1993)). One approach to solve this problem has been to use antigen detection assays that detect a cell wall polysaccharide in the urine. This assay is much more sensitive but unfortunately has false positives in 12% of adults and up to 60% of children. This is because the assay target is sometimes present in the urine because of nasal colonization with pneumococci in patients without pneumococcal disease in their lungs or blood. Thus, also provided herein are methods of detecting pneumococcal pneumonia in a subject comprising detecting in a sample from the subject the presence of PhtD, wherein the presence of PhtD indicates pneumococcal bacteria in the subject. PhtD concentrations can be assayed in biological sample such as a bodily fluid by methods known to those of skill in the art. Suitable body fluids for use in the methods include but are not limited to blood, serum, mucous and urine.

Also described herein is a method of reducing the risk of a pneumococcal infection in a subject comprising administering to the subject an immunogenic fragment of PhtD, or a derivative or variant thereof. Pneumococcal infections include, for example, meningitis, otitis media, pneumonia, sepsis, or hemolytic uremia. Thus, the risk of any one or more of these infections may be reduced by the methods described herein.

The compositions comprising a PhtD polypeptide may be administered orally, parenterally (e.g., intravenously), intramuscularly, intraperitoneally, transdermally or topically, including intranasal administration or administration to any part of the respiratory system. As used herein, administration to the respiratory system means delivery of the compositions into the nose and nasal passages through one or both of the nares or through the mouth, including delivery by a spraying mechanism or droplet mechanism, through aerosolization or intubation.

The exact amount of the compositions and PhtD polypeptide required will vary from subject to subject, depending on the species, age, weight and general condition of the subject, the polypeptide used, and its mode of administration. Thus, it is not possible to specify an exact amount for every composition. However, an appropriate amount can be determined by one of ordinary skill in the art given the description herein. Furthermore, multiple doses of the PhtD polypeptide may be used including, for example, in a prime and boost regimen.

The term "antibody" or "antibodies" includes whole or fragmented antibodies in unpurified or partially purified form (i.e., hybridoma supernatant, ascites, polyclonal antisera) or in purified form. A "purified" antibody is one that is separated from at least about 50% of the proteins with which it is initially found (i.e., as part of a hybridoma supernatant or ascites preparation). Preferably, a purified antibody is separated from at least about 60%, 75%, 90%, or 95% of the proteins with which it is initially found. Suitable derivatives may include fragments (i.e., Fab, $Fab_2$ or single chain antibodies (Fv for example)), as are known in the art. The antibodies may be of any suitable origin or form including, for example, murine (i.e., produced by murine hybridoma cells), or expressed as humanized antibodies, chimeric antibodies, human antibodies, and the like.

Methods of preparing and utilizing various types of antibodies are well-known to those of skill in the art and would be suitable in practicing the present invention (see, for example, Harlow, et al. *Antibodies: A Laboratory Manual*, Cold Spring Harbor Laboratory, 1988; Harlow, et al. *Using Antibodies: A Laboratory Manual, Portable Protocol No. 1*, 1998; Kohler and Milstein, Nature, 256:495 (1975); Jones et al. Nature, 321:522-525 (1986); Riechmann et al. Nature, 332:323-329 (1988); Presta, Curr. Op. Struct. Biol., 2:593-596 (1992); Verhoeyen et al., Science, 239:1534-1536 (1988); Hoogenboom et al., J. Mol. Biol., 227:381 (1991); Marks et al., J. Mol. Biol., 222:581 (1991); Cole et al., Monoclonal Antibodies and Cancer Therapy, Alan R. Liss, p. 77 (1985); Boerner et al., J. Immunol., 147(1):86-95 (1991); Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995); as well as U.S. Pat. Nos. 4,816,567; 5,545,807; 5,545,806; 5,569,825; 5,625,126; 5,633,425; and, 5,661,016). In certain applications, the antibodies may be contained within hybridoma supernatant or ascites and utilized either directly as such or following concentration using standard techniques. In other applications, the antibodies may be further purified using, for example, salt fractionation and ion exchange chromatography, or affinity chromatography using Protein A, Protein G, Protein A/G, and/or Protein L ligands covalently coupled to a solid support such as agarose beads, or combinations of these techniques. The antibodies may be stored in any suitable format, including as a frozen preparation (i.e., −20° C. or −70° C.), in lyophilized form, or under normal refrigeration conditions (i.e., 4° C.). When stored in liquid form, it is preferred that a suitable buffer such as Tris-buffered saline (TBS) or phosphate buffered saline (PBS) is utilized.

Exemplary antibodies include monoclonal antibodies. Other antibodies, including ascites, polyclonal antisera or other preparations containing such antibodies, for example, are also contemplated.

Preparations including such antibodies may include unpurified antibody as found in a hybridoma supernatant or ascites preparation, partially purified preparations, or purified preparations. Thus, provided herein are antibody preparations containing the antibodies purfied to about 50%, 60%, 75%, 90%, or 95% purity. Typically, such preparations include a buffer such as phosphate- or tris-buffered saline (PBS or TBS, respectively). Also provided are derivatives of such antibodies including fragments (Fab, Fab$_2$ or single chain antibodies (Fv for example)), humanized antibodies, chimeric antibodies, human antibodies, and the like. The genes encoding the variable and hypervariable segments of the antibodies may also be isolated from the hybridomas expressing the same cloned into expression vectors to produce certain antibody preparations (i.e., humanized antibodies). Methods for producing such preparations are well-known in the art.

The skilled artisan has many suitable techniques for using the antibodies described herein to identify biological samples containing proteins that bind thereto. For instance, the antibodies may be utilized to isolate PhtD protein using, for example, immunoprecipitation or other capture-type assay. This well-known technique is performed by attaching the antibody to a solid support or chromatographic material (i.e., a bead coated with Protein A, Protein G and/or Protein L). The bound antibody is then introduced into a solution either containing or believed to contain the PhtD protein. PhtD protein then binds to the antibody and non-binding materials are washed away under conditions in which the PhtD protein remains bound to the antibody. The bound protein may then be separated from the antibody and analyzed as desired. Similar methods for isolating a protein using an antibody are well-known in the art.

The antibodies may also be utilized to detect PhtD protein within a biological sample. For instance, the antibodies may be used in assays such as, for example, flow cytometric analysis, ELISA, immunoblotting (i.e., Western blot), in situ detection, immunocytochemistry, and/or immunohistochemistry. Methods of carrying out such assays are well-known in the art.

To assist the skilled artisan in using the antibodies, the same may be provided in kit format. A kit including 1B12, 4D5, and/or 9E11, optionally including other components necessary for using the antibodies to detect cells expressing PhtD is provided. The antibodies of the kit may be provided in any suitable form, including frozen, lyophilized, or in a pharmaceutically acceptable buffer such as TBS or PBS. The kit may also include other reagents required for utilization of the antibodies in vitro or in vivo such as buffers (i.e., TBS, PBS), blocking agents (solutions including nonfat dry milk, normal sera, Tween-20 Detergent, BSA, or casein), and/or detection reagents (i.e., goat anti-mouse IgG biotin, streptavidin-HRP conjugates, allophycocyanin, B-phycoerythrin, R-phycoerythrin, peroxidase, fluors (i.e., DyLight, Cy3, Cy5, FITC, HiLyte Fluor 555, HiLyte Fluor 647), and/or staining kits (i.e., ABC Staining Kit, Pierce)). The kits may also include other reagents and/or instructions for using the antibodies in commonly utilized assays described above such as, for example, flow cytometric analysis, ELISA, immunoblotting (i.e., western blot), in situ detection, immunocytochemistry, immunohistochemistry.

In one embodiment, the kit provides antibodies in purified form. In another embodiment, antibodies are provided in biotinylated form either alone or along with an avidin-conjugated detection reagent (i.e., antibody). In another embodiment, the kit includes a fluorescently labelled antibody which may be used to directly detect PhtD protein. Buffers and the like required for using any of these systems are well-known in the art and may be prepared by the end-user or provided as a component of the kit. The kit may also include a solid support containing positive- and negative-control protein and/or tissue samples. For example, kits for performing spotting or western blot-type assays may include control cell or tissue lysates for use in SDS-PAGE or nylon or other membranes containing pre-fixed control samples with additional space for experimental samples. Kits for visualization of PhtD in cells on slides may include pre-formatted slides containing control cell or tissue samples with additional space for experimental samples.

The antibodies and/or derivatives thereof may also be incorporated into compositions of the invention for use in vitro or in vivo. The antibodies or derivatives thereof may also be conjugated to functional moieties such as cytotoxic drugs or toxins, or active fragments thereof such as diphtheria A chain, exotoxin A chain, ricin A chain, abrin A chain, curcin, crotin, phenomycin, enomycin, among others. Functional moieties may also include radiochemicals.

It is also possible to use the antibodies described herein as reagents in drug screening assays. The reagents may be used to ascertain the effect of a drug candidate on the presence of *Streptococcus* sp. bacteria in a biological sample of a patient, for example. The expression profiling technique may be combined with high throughput screening techniques to allow rapid identification of useful compounds and monitor the effectiveness of treatment with a drug candidate (see, for example, Zlokarnik, et al., Science 279, 84-8 (1998)). Drug candidates may be chemical compounds, nucleic acids, proteins, antibodies, or derivatives therefrom, whether naturally occurring or synthetically derived. Drug candidates thus identified may be utilized, among other uses, as pharmaceutical compositions for administration to patients or for use in further screening assays.

The antibodies described herein may be prepared as injectable preparation, such as in suspension in a non-toxic parenterally acceptable diluent or solvent. Suitable vehicles and solvents that may be utilized include water, Ringer's solution, and isotonic sodium chloride solution, TBS and PBS, among others. In certain applications, the antibodies are suitable for use in vitro. In other applications, the antibodies are suitable for use in vivo. The preparations suitable for use in either case are well-known in the art and will vary depending on the particular application.

It must be noted that, as used in the specification and the appended claims, the singular forms "a", "an", and "the" include plural referents unless the context clearly dictates otherwise. Thus, for example, reference to an antigenic fragment includes mixtures of antigenic fragments, reference to a pharmaceutical carrier or adjuvant includes mixtures of two or more such carriers or adjuvants.

As used herein, a subject or a host is meant to be an individual. The subject can include domesticated animals, such as cats and dogs, livestock (e.g., cattle, horses, pigs, sheep, and goats), laboratory animals (e.g., mice, rabbits, rats, guinea pigs) and birds. In one aspect, the subject is a mammal such as a primate or a human.

Optional or optionally means that the subsequently described event or circumstance can or cannot occur, and that the description includes instances where the event or circumstance occurs and instances where it does not. For example, the phrase optionally the composition can comprise a combination means that the composition may comprise a combination of different molecules or may not include a combination such that the description includes both the combination and the absence of the combination (i.e., individual members of the combination).

Ranges may be expressed herein as from about one particular value, and/or to about another particular value. When such a range is expressed, another aspect includes from the one particular value and/or to the other particular value. Similarly, when values are expressed as approximations, by use of the antecedent about, it will be understood that the particular value forms another aspect. It will be further understood that the endpoints of each of the ranges are significant both in relation to the other endpoint, and independently of the other endpoint.

When the terms prevent, preventing, and prevention are used herein in connection with a given treatment for a given condition (e.g., preventing infection by Streptococcus sp.), it is meant to convey that the treated patient either does not develop a clinically observable level of the condition at all, or develops it more slowly and/or to a lesser degree than he/she would have absent the treatment. These terms are not limited solely to a situation in which the patient experiences no aspect of the condition whatsoever. For example, a treatment will be said to have prevented the condition if it is given during exposure of a patient to a stimulus that would have been expected to produce a given manifestation of the condition, and results in the patient's experiencing fewer and/or milder symptoms of the condition than otherwise expected. A treatment can "prevent" infection by resulting in the patient's displaying only mild overt symptoms of the infection; it does not imply that there must have been no penetration of any cell by the infecting microorganism.

Similarly, reduce, reducing, and reduction as used herein in connection with the risk of infection with a given treatment (e.g., reducing the risk of a pneumococcal infection) refers to a subject developing an infection more slowly or to a lesser degree as compared to a control or basal level of developing an infection in the absence of a treatment (e.g., administration of an immunogenic polypeptide). A reduction in the risk of infection may result in the patient's displaying only mild overt symptoms of the infection or delayed symptoms of infection; it does not imply that there must have been no penetration of any cell by the infecting microorganism.

Further embodiments and characterizations of the present invention are provided in the following non-limiting examples.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Provided herein, in one embodiment of the invention are isolated, truncated PhtD polypeptides from Streptococcus pneuomoniae serotype 6 strain 14453 deposited on Jun. 27, 1997 as ATCC 55987 and/or having sequence as set forth in SEQ ID NO. 1. The PhtD truncations described in this invention encompass regions of the protein that are both similar and dissimilar to regions in PhtB, and thus contain potential cross-reactive and unique epitopes, respectively. The truncated proteins are expressed in Escherichia coli as recombinant His-tagged derivatives to facilitate purification, and subsequently purified using $Ni^{2+}$-NTA affinity chromatography.

Example 1

Cloning and Production of Recombinant PhtD Truncated Proteins

This example describes the cloning of truncated versions of phtD from Streptococcus pneumoniae serotype 6 strain 14453 into plasmid pET28a(+) so that the expressed product has an N-terminal 6xHis-tag. The truncated forms of PhtD can also be expressed without the N-terminal 6xHis-tag as illustrated in SEQ ID NOS. 2, 3 and 4 (protein) as well as SEQ ID NOS. 5, 7 and 9 (DNA).

The primers used in amplifying the sequences described herein are shown in Table 3:

TABLE 3

PCR Primers

| Primer Name/Number | Sequence 5'→3', restriction sites underlined |
|---|---|
| Spn0215 | CTAGCCATGGGACATCATCATCATCATCACTGGGTACCAGATTCAAGACCAG (SEQ ID NO. 11) |
| Spn0216 | CTAGCCATGGGACATCATCATCATCATCACGTCAAGTACTATGTCGAACATCC (SEQ ID NO. 12) |
| Spn0217 | CTAGCCATGGGACATCATCATCATCATCACCATGTTCGTAAAAATAAGGTAGAC (SEQ ID NO. 13) |
| Spn0176 | TGGCCTCGAGTTACTACTGTATAGGAGCCGGTT (SEQ ID NO. 14) |

Truncation # 1

Briefly, the phtD T1 gene was PCR amplified from the *S. pneumoniae* serotype 6 strain 14453 genome using a High Fidelity Advantage 2 polymerase (BD). PCR primers Spn0215 and Spn0176 introduced NcoI and XhoI restriction sites into the 5' and 3' ends, respectively (see Table 3). The 5' primer, Spn0215, also introduced the N-terminal His-tag. The PCR product was purified using a QIAquick PCR purification kit (Qiagen) and subsequently run on an agarose gel for purification using the QIAEX gel extraction kit (Qiagen). The PCR product and the pET28a(+) vector (Novagen) were both digested with NcoI and XhoI and subsequently purified from an agarose gel using the QIAEX gel extraction kit (Qiagen). The digested vector and gene were then ligated together using a T4 DNA ligase (Invitrogen). The ligation mixture was transformed into chemically competent *E. coli* DH5a and positive clones were selected by plating on Luria agar containing 50 ug/ml kanamycin. Four colonies per construct were chosen and plasmid DNA was isolated using the QIAprep Spin Miniprep kit (Qiagen). NcoI/XhoI digests were performed to determine which clones had the correct size of fragments. All four clones were correct according to restriction analysis, and Midiprep DNA was then isolated from one positive clone (#1) using the QIAfilter Plasmid Midi kit (Qiagen) and was DNA sequenced to ensure no cloning artifacts were introduced. This clone was designated pBAC30.

The PhtD T1 was expressed in *E. coli* BL21 (DE3) at a high level, as seen by an intense band of the correct size of approximately 56.1 kDa in an SDS-PAGE gel. Protein expression was induced for 2 hours with 1 mM IPTG.

Truncation # 2

The phtD T2 gene was also PCR amplified from the *S. pneumoniae* serotype 6 strain 14453 genome using a High Fidelity Advantage 2 polymerase (BD). PCR primers Spn0216 and Spn0176 introduced NcoI and XhoI restriction sites into the 5' and 3' ends, respectively (see Table 3). The 5' primer, Spn0216, also introduced the N-terminal His-tag. The PCR product was purified using a QIAquick PCR purification kit (Qiagen) and subsequently run on an agarose gel for purification using the QIAEX gel extraction kit (Qiagen). The PCR product and the pET28a(+) vector (Novagen) were both digested with NcoI and XhoI and subsequently purified from an agarose gel using the QIAEX gel extraction kit (Qiagen). The digested vector and gene were then ligated together using a T4 DNA ligase (Invitrogen). The ligation mixture was transformed into chemically competent *E. coli* DH5a and positive clones were selected by plating on Luria agar containing 50µg/ml kanamycin. Plasmid DNA was isolated from selected clones using the QIAprep Spin Miniprep kit (Qiagen). NcoI/XhoI digests were performed to determine which clones had the correct size of fragments. Midiprep DNA was then isolated from one positive clone using the QIAfilter Plasmid Midi kit (Qiagen) and sequenced to ensure no cloning artifacts were introduced. This clone was designated pBAC31.

The PhtD T2 protein was expressed in *E. coli* BL21 (DE3) at a high level, as seen by an intense band running at approximately 19.3 kDa in an SDS-PAGE gel. Protein expression was induced for 2 hours with 1 mM IPTG.

Truncation # 3

The phtD T3 gene was also PCR amplified from the *S. pneumoniae* serotype 6 strain 14453 genome using a High Fidelity Advantage 2 polymerase (BD). Spn0217 and Spn0176 introduced NcoI and XhoI restriction sites into the 5' and 3' ends, respectively (see Table 3). The 5' primer, Spn0217, also introduced the N-terminal 6xHis-tag. The PCR product was purified using a QIAquick PCR purification kit (Qiagen) and subsequently run on an agarose gel for purification using the QIAEX gel extraction kit (Qiagen). The PCR product and the pET28a(+) vector (Novagen) were both digested with NcoI and XhoI and subsequently purified from an agarose gel using the QIAEX gel extraction kit (Qiagen). The digested vector and gene were then ligated together using a T4 DNA ligase (Invitrogen). The ligation mixture was transformed into chemically competent *E. coli* DH5a and positive clones were selected by plating on Luria agar containing 50 µg/ml kanamycin. Colonies were chosen and plasmid DNA was isolated using the QIAprep Spin Miniprep kit (Qiagen). NcoI/XhoI digests were performed to determine which clones had the correct size of fragments. Midiprep DNA was then isolated from one positive clone using the QIAfilter Plasmid Midi kit (Qiagen) and sequenced to ensure no cloning artifacts were introduced. This clone was designated pBAC32.

The PhtD T3 protein was expressed in *E. coli* BL21 (DE3) at a high level, as seen by an intense band running at approximately 16.7 kDA in an SDS-PAGE gel. Protein expression was induced for 2 hours with 1 mM IPTG.

The amino acid sequences of the truncated polypeptides are shown below:

```
PhtD truncation 1 including His tag
(underlined) expressed from pBAC30:
                                 (SEQ ID NO. 15)
MGHHHHHHWVPDSRPEQPSPQSTPEPSPSPQPAPNPQPAPSNPIDEKLVK

EAVRKVGDGYVFEENGVSRYIPAKDLSAETAAGIDSKLAKQESLSHKLGA

KKTDLPSSDREFYNKAYDLLARIHQDLLDNKGRQVDFEALDNLLERLKDV

PSDKVKLVDDILAFLAPIRHPERLGKPNAQITYTDDEIQVAKLAGKYTTE

DGYIFDPRDITSDEGDAYVTPHMTHSHWIKKDSLSEAERAAAQAYAKEKG

LTPPSTDHQDSGNTEAKGAEAIYNRVKAAKKVPLDRMPYNLQYTVEVKNG

SLIIPHYDHYHNIKFEWFDEGLYEAPKGYTLEDLLATVKYYVEHPNERPH

SDNGFGNASDHVRKNKVDQDSKPDEDKEHDEVSEPTHPESDEKENHAGLN

PSADNLYKPSTDTEETEEEAEDTTDEAEIPQVENSVINAKIADAEALLEK

VTDPSIRQNAMETLTGLKSSLLLGTKDNNTISAEVDSLLALLKESQPAPI

Q

PhtD truncation 2 including His tag
(underlined) expressed from pBAC31:
                                 (SEQ ID NO. 16)
MGHHHHHHVKYYVEHPNERPHSDNGFGNASDHVRKNKVDQDSKPDEDKEH

DEVSEPTHPESDEKENHAGLNPSADNLYKPSTDTEETEEEAEDTTDEAEI

PQVENSVINAKIADAEALLEKVTDPSIRQNAMETLTGLKSSLLLGTKDNN

TISAEVDSLLALLKESQPAPIQ

PhtD truncation 3 including His tag
(underlined) expressed from pBAC32:
                                 (SEQ ID NO. 17)
MGHHHHHHVRKNKVDQDSKPDEDKEHDEVSEPTHPESDEKENHAGLNPS

ADNLYKPSTDTEETEEEAEDTTDEAEIPQVENSVINAKIADAEALLEKVT

DPSIRQNAMETLTGLKSSLLLGTKDNNTISAEVDSLLALLKESQPAPIQ
```

Structural Characterization of PhtD Truncations and Comparison to Full-length PhtD Purified PhtD truncations 1, 2, and 3 were each characterized by biochemical and biophysical means and the results obtained were compared with characterization data obtained from analysis of full-length PhtD protein (lacking signal sequence) lots. The following assays were performed: circular dichrosim (CD) spectroscopy, intrinsic fluorescence spectroscopy, analytical ultracentrifugation (AUC), size-exclusion chromatography with multi-angle light scattering detection (SEC-MALS), and differential scanning calorimetry (DSC). Results from these analyses are summarized in Table 4 below.

TABLE 4

Summary of characterization results for PhtD and PhtD truncations

| Test | PhtD Full-Length | PhtD Truncation 1 | PhtD Truncation 2 | PhtD Truncation 3 |
|---|---|---|---|---|
| CD spectroscopy | Mixed α-helix/β-sheet secondary structure | Mixed α-helix/β-sheet secondary structure | Mainly α-helix secondary structure | Mainly α-helix secondary structure |
| Fluorescence spectroscopy | Emission max = 347-349 nm* | Emission max = 349 nm* | Not determined due to low signal | Not determined due to low signal |
| AUC | Monomeric Highly extended solution structure | Monomeric Extended solution structure | Monomeric Compact solution structure | Monomeric Compact solution structure |
| SEC-MALS | Monomeric | Monomeric | Monomeric | Monomeric |
| DSC | 3 transitions $T_m = 58.0°$ C., $72.1°$ C., $89.0°$ C.~ | 2 transitions $T_m = 62.1°$ C., $82.8°$ C. | 1 transition $T_m = 85.3°$ C. | 1 transition $T_m = 85.5°$ C. |

*At 280 nm and 295 nm excitation frequencies
~$T_m$, thermal transition midpoint Based on the characterization results summarized in Table 4, PhtD truncation 1 has a similar, though not identical, overall solution structure to full-length PhtD, while the structures of PhtD truncations 2 and 3 are different. The multiple thermal transitions observed in DSC analysis of PhtD are suggestive of the presence of multiple (i.e. three) domains. DSC results for PhtD truncation 1 show 2 transitions, suggesting that the truncation has removed one of these domains. PhtD truncations 2 and 3 have similar overall structures, and DSC results show the presence of a single domain which is highly thermally stable. These results show that the truncations are in a folded conformation.

Example 2

Monoclonal Antibodies

Monoclonal antibodies were generated to a number of pneumococcal histidine triad (Pht) proteins (i.e. PhtD, PhtA, PhtB, PhtE) by ImmunoPrecise (Victoria, BC, Canada). To generate the monoclonals, mice were immunized with the various proteins and the hyrbidomas secreting antibodies with specificity therefore were isolated using standard procedures. A number of hybridoma clones were generated for each of PhtD, PhtA, PhtB and PhtE.

With respect to PhtD, mice were immunized with recombinantly produced PhtD full-length protein (his-tagged and lacking signal sequence). The recombinantly produced PhtD protein was derived from the *S. pneumoniae* strain TIGR4 (deposited with the American Type Culture Collection, ATCC BAA-334). The amino acid sequence of the PhtD protein used to immunize the mice, SEQ ID NO:24 is set out below and the corresponding nucleotide sequence is SEQ ID NO:23.

Recombinant PhtD Protein Sequence:
(SEQ ID NO: 24)
MGSSHHHHHHSSGLVPRGSHMASMTGGQQMGRGSSYELGRHQAGQVKKES

NRVSYIDGDQAGQKAENLTPDEVSKREGINAEQIVIKITDQGYVTSHGDH

YHYYNGKVPYDAIISEELLMKDPNYQLKDSDIVNEIKGGYVIKVDGKYYV

YLKDAAHADNIRTKEEIKRQKQEHSHNHGGGSNDQAVVAARAQGRYTTDD

GYIFNASDIIEDTGDAYIVPHGDHYHYIPKNELSASELAAAEAYWNGKQG

SRPSSSSSYNANPAQPRLSENHNLTVTPTYHQNQGENISSLLRELYAKPL

SERHVESDGLIFDPAQITSRTARGVAVPHGNHYHFIPYEQMSELEKRIAR

IIPLRYRSNHWVPDSRPEQPSPQSTPEPSPSPQPAPNPQPAPSNPIDEKL

VKEAVRKVGDGYVFEENGVSRYIPAKDLSAETAAGIDSKLAKQESLSHKL

GAKKTDLPSSDREFYNKAYDLLARIHQDLLDNKGRQVDFEALDNLLERLK

DVPSDKVKLVDDILAFLAPIRHPERLGKPNAQITYTDDEIQVAKLAGKYT

TEDGYIFDPRDITSDEGDAYVTPHMTHSHWIKKDSLSEAERAAAQAYAKE

KGLTPPSTDHQDSGNTEAKGAEAIYNRVKAAKKVPLDRMPYNLQYTVEVK

NGSLIIPHYDHYHNIKFEWFDEGLYEAPKGYTLEDLLATVKYYVEHPNER

PHSDNGFGNASDHVRKNKVDQDSKPDEDKEHDEVSEPTHPESDEKENHAG

LNPSADNLYKPSTDTEETEEEAEDTTDEAEIPQVENSVINAKIADAEALL

EKVTDPSIRQNAMETLTGLKSSLLLGTKDNNTISAEVDSLLALLKESQPA

PIQ a. Cross-Reactivity

The cross-reactivity of each of the monoclonal antibodies generated to the different Pht proteins was assessed by ELISA using supernatants from the hybridomas. The results of the ELISA are set out below in Table 5. Each of the monoclonal antibodies generated (e.g. PhtD) was screened in the ELISA for reactivity to the particular Pht protein to which it was raised (identified in Table 4 as "Self") and to combinations of Pht proteins (e.g. PhtA and PhtE, are identified in Table 5 as "A,E"). The total number of hybridoma clones generated for each Pht protein is noted in Table 5 in brackets under the applicable Pht protein in the "Immunizing Protein" column (e.g. 14 hybridoma clones were generated to PhtD). The Pht proteins used in the screen were recombinant whole protein.

TABLE 5

| Immunizing Protein | Number of clones specific for different Pht proteins | | | | | | | | |
|---|---|---|---|---|---|---|---|---|---|
| | Self | A, E | B, D | B, E | D, E | A, B, D | A, B, E | B, D, E | A, B, D, E |
| PhtD (14 total) | 4 | — | 3 | 0 | 0 | 6 | — | 0 | 1 |
| PhtB (69 total) | 9 | — | 37 | 0 | — | 15 | 0 | 2 | 6 |
| PhtA (48 total) | 19 | — | — | — | — | 5 | 0 | — | 24 |
| PhtE (72 total) | 50 | 6 | — | 1 | 7 | — | 2 | 0 | 6 |

On the basis of the results from the cross-reactivity screen (by ELISA), a number of antibodies were selected for further analysis including, hybridoma clones 9E11, 4D5 and IB12. While each of clones 9E11, 4D5 and IB12 were generated to PhtD, clone 9E11 was determined in the cross-reactivity screen, as having specificity to PhtD only, whereas clones 4D5 and IB12 each were found to have specificity for PhtA, B and D.

b. Epitope Mapping

Epitope mapping was performed using denaturing SDS-PAGE/Western blot. It was determined that clone 4D5 and 9E11 each produce mAbs that bind to linear epitopes of the Truncation 3 fragment of PhtD. Proteolytic digestion of the Truncation 3 fragment of PhtD followed by Western blot showed that the linear epitope recognized by mAb 9E11 lies within a sequence corresponding to amino acids 1 to 101 (SEQ ID NO:26) of the Truncation 3 fragment (and the corresponding amino acid sequence of the full-length PhtD protein). Further testing of the mAbs of each clone (i.e. clones 9E11, 4D5 and IB12) by ELISA using Truncations 1, 2 and 3 of PhtD confirmed the specificity ascertained for each clone by Western blots and identified mAb clone (1B12) as having specificity for the T3 truncation.

c. Passive Protection

In a further embodiment of the present invention, the mAbs produced by each of clones 9E11, 4D5 and IB12 were assessed for their ability to protect animals from challenge with S. pneumoniae.

An initial experiment was performed to test the ability of antibodies each raised in rabbits against either full-length PspA, PhtB or PhtD to provide passive protection against S. pneumoniae infection. In this study, groups of CBA/n mice were pre-treated with an intraperitoneal dose of rabbit anti-PspA, anti-PhtB, or anti-PhtD sera (diluted 1:10) one hour prior to intravenous administration of 50 cfu of S. pneumoniae strain A66.1. For each group that had been pre-treated with antibody (i.e. either PspA, PhtB or PhtD), 100% of the animals survived. By contrast, 1/20 of the animals that had been pre-treated with prebleed rabbit PspA serum survived, 0/10 of the animals that had been pre-treated with prebleed rabbit PhtB serum survived and 1/25 of the animals that had been pre-treated with prebleed rabbit PhtD serum survived.

The passive protection studies conducted utilized a previously developed Passive Protection Model. The Model uses CBA/CaHN-Btkxid/J mice, which are known to be highly susceptible to infection by S. pneumoniae and involves the intraperitoneal administration of the antibody under study one hour prior to the intravenous administration of 50 cfu of S. pneumonaie strain A66.1. The challenge dose administered is verified pre and post challenge. Mortality is monitored for 14 days and blood from surviving mice is plated to confirm bacterial clearance.

In one experiment, the mAbs produced by clones 4D5 and 9E11 were each tested using the passive immunization model. Groups of 5 mice were used. Three groups were intraperitoneally administered 400 µg of either 4D5 mAb in phosphate-buffered saline (PBS), 9E11 mAb in PBS, or PBS (i.e. negative control group). The positive control group was administered rabbit anti-PhtD. Each group was administered a challenge dose of 50 cfu of S. pneumoniae strain A66.1. Eighty percent of the animals immunized with the mAb produced by clone 4D5 survived the challenge dose and one hundred percent of the animals immunized with mAb 9E11 survived the challenge dose. No animals survived following "immunization" with PBS whereas one hundred per cent of the animals immunized with rabbit anti-PhtD suriviied the challenge dose.

In a separate experiment, the mAb IB12 was tested using the passive immunization model. 400 µg of 1B12 mAb in PBS was administered via the intraperitoneal route followed by administration of a challenge dose of 50 cfu of S. pneumoniae strain A66.1. In respect of the group that had been immunized with mAb IB12, one hundred percent of the animals survived the challenge dose through day 3 and eighty percent of the animals survived the challenge dose through day 14 (i.e. the limits of testing). None of the animals in the group "immunized" with PBS survived past day 1 whereas each of the animals in the positive control group (i.e. immunized with rabbit anti-PhtD sera) survived the challenge dose through day 14.

Dosing studies were also performed. Using the same challenge model, animals were immunized with 400 µg, 200 µg, 100 µg or 50 µg mAb 9E11 in PBS one hour prior to the administration of a challenge dose of 50 cfu of S. pneumoniae strain A66.1. The negative control group was administered PBS prior to challenge and the positive control group was administered rabbit anti-PhtD sera (in a 1:10 dilution) prior to challenge. After 14 days, 60% of mice survived following the 400 µg dose; 20% survived following the 200 µg dose; and no animals survived following the 100 µg or 50 µg doses. With respect to the group administered the 400 µg dose, survival dropped to 80% at day 6, and to 60% at day 9. With respect to the group administered the 200 µg dose, survival dropped to 60% at day 3, and to 20% at day 5. In regards to the group administered the 100 µg dose, survival dropped to 20% at day 2 and to 0% at day 3. Thus, an increase in 14-day survival was observed for both the group administered the 400 µg (60% survival) dose and the group administered the 200 µg dose (20% survival).

A similar dosing study was performed using mAb 4D5. Animals were immunized with 400 µg, 200 µg, 100 µg or 50 µg mAb 4D5 in PBS one hour prior to administration of the administration of challenge dose of 50 cfu of *S. pneumoniae* strain A66.1. After 14 days, 100% of mice survived following the 400 mg dose and none survived the lower doses or the control (PBS). One hundred percent of the animals survived to day 2 following the 200 µg dose; 60% survived to day 2, and 20% survived to day 3. Thus, an increase in 14-day survival was observed in both the group administered the 400 µg (100% survival) dose and the group administered the 200 µg dose (20% survival to day 3).

d. Synergistic Effect of mAbs

A study was performed to test the ability of the mAbs to act synergistically. The same Passive Protection Model was utilized as in the previous studies. Eight groups of mice (with 5 in each) were utilized and administered prior to the challenge dose either 100 µm 4D5 mAbs, 200 µg 4D5 mAbs, 100 µg 9E11 mAbs, 200 µg 9E11 mAbs, 200 µg of a pool consisting of 100 µg of each of 9E11 and 4D5, PBS (i.e. negative control), rabbit anti-PspA sera (i.e. positive control) or 400 µg of IB12 mAbs. It was found that a 200 µg total dose containing 100 µg each of the 4D5 and 9E11 antibodies provided 100% protection to 14 days (i.e. the limits of the test). In contrast, 200 µg of mAbs 4D5 or 9E11 alone provided only 20% and 40% survival at day 14, respectively. A 100 µg dose of 4D5 provided 100% survival through day 1 (as did PBS) and 60% survival through day 2 which dropped to 20% survival at day 3 (which was sustained through day 14). A 100 µg dose of mAb 9E11 provided 100% survival through day 1 (as did PBS), 80% survival through day 2, 60% survival through day 3 and 20% survival from days 4-6, which then dropped to zero. A subsequent experiment, the data from which is set out in Table 6 below, confirmed this synergistic effect. In this study, animal groups were administered doses of varying concentrations of the mAb pool (i.e. pool of equal amounts of 9E11 and 4D5 mAbs).

by *S. pneumoniae*. These experiments also demonstrate a surprisingly synergistic effect resulting from the combined dosing of mAbs 4D5 and 9E11 over the expected additive effect of combining the individual antibodies. The monoclonal antibodies described herein may be used separately or in combination.

While the present invention has been described in terms of the preferred embodiments, it is understood that variations and modifications will occur to those skilled in the art. Therefore, it is intended that the appended claims cover all such equivalent variations that come within the scope of the invention as claimed.

REFERENCES

Adamou J E, Heinrichs J H, Erwin A L, Walsh W, Gayle T, Dormitzer M, Dagan R, Brewah Y A, Barren P, Lathigra R, Langermann S, Koenig S, Johnson S. 2001. "Identification and Characterization of a Novel Family of Pneumococcal Proteins That Are Protective against Sepsis." Infect Immun. 69:949-958.

Hamel J, Charland N, Pineau I, Ouellet C, Rioux S, Martin D, Brodeur B R. 2004. "Prevention of Pneumococcal Disease in Mice Immunized with Conserved Surface-Accessible Proteins." Infect Immun. 72:2659-2670.

Ogunniyi A D, Grabowicz M, Briles D E, Cook J, Paton J C. 2007. "Development of a vaccine against invasive pneumococcal disease based on combinations of virulence proteins of *Streptococcus pneumoniae*." Infect Immun. 75:350-357.

Zhang Y, Masi A W, Barniak V, Mountzouros K, Hostetter M K, Green B A. 2001. "Recombinant PhpA protein, a unique histidine motif-containing protein from *Streptococcus pneumoniae*, protects mice against intranasal pneumococcal disease." Infect Immun. 69: 3827-3836.

Guilmi, et al. New approaches towards the identification of antibiotic and vaccine targets in *Streptococcus pneumoniae*. EMBO reports 3, 8, 728-734 (2002)

U.S. Pat. No. 7,122,194. Johnson, et. al. Oct. 17, 2006. Title: Vaccine compositions comprising *Streptococcus pneumoniae* polypeptides having selected structural motifs

TABLE 6*

| Day | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| PBS | 100 | 0 | 0 | 0 | 0 | 0 | 0 | 0 | 0 | 0 | 0 | 0 | 0 | 0 |
| PspA | 100 | 100 | 100 | 100 | 100 | 100 | 100 | 100 | 100 | 100 | 100 | 100 | 100 | 100 |
| 200P | 100 | 100 | 100 | 100 | 100 | 100 | 100 | 100 | 100 | 100 | 100 | 100 | 100 | 100 |
| 100P | 100 | 100 | 100 | 80 | 60 | 60 | 60 | 60 | 60 | 60 | 60 | 60 | 60 | 60 |
| 50P | 100 | 100 | 80 | 60 | 40 | 20 | 0 | 0 | 0 | 0 | 0 | 0 | 0 | 0 |
| 25P | 100 | 60 | 20 | 0 | 0 | 0 | 0 | 0 | 0 | 0 | 0 | 0 | 0 | 0 |

*PBS: phosphate-buffered saline; PspA: anti-full length PspA; 200P: 200 µg pool of 4D5 and 9E11; 100P: 100 µg pool of 4D5 and 9E11; 50P: 50 µg pool of 4D5 and 9E11; 25P: 25 µg pool of 4D5 and 9E11.

As shown in Table 6, the synergistic effect was observed for each dose. Although the 25 µg dose was not previously tested, the 25 µg pooled dose provided 20% survival to day 3. In previous experiments, a 50 µg dose of either mAb 4D5 or 9E11 had essentially the same result as did the PBS dose (i.e. negative control).

These experiments demonstrate that the 4D5 and 9E11 mAbs may each be used to provide protection from infection U.S. Pat. No. 6,582,706. Johnson, et. al. Jun. 24, 2003. Title: Vaccine compositions comprising *Streptococcus pneumoniae* polypeptides having selected structural motifs United States Patent Application 20050214329 Laferriere, Craig Anthony Joseph; et al. Sep. 29, 2005 Title: Vaccine United States Patent Application 20040081662 Hermand, Philippe ; et al. Apr. 29, 2004 Title: Vaccine

What is claimed is:

1. A method for treating infection by *Streptococcus* species (sp.) bacteria in a host comprising administering to the host at least two monoclonal antibodies having specificity for SEQ ID NO.:4, wherein at least one of said antibodies has specificity for an epitope within SEQ ID NO.:26.

2. The method of claim 1 wherein at least one of the antibodies is cross-reactive against *Streptococcus pneumoniae* pneumococcal histidine triad protein A, pneumococcal histidine triad protein B, or pneumococcal histidine triad protein D.

3. The method of claim 1 or 2 wherein at least two of the monoclonal antibodies are administered to the host in approximately the same dose.

4. The method of any one of claim 1, or 2, wherein a protective effect against infection by *Streptococcus* sp. bacteria is provided to the host by the antibodies.

5. The method of any one of claim 1, or 2, wherein a protective effect against infection by *Streptococcus* sp. bacteria is provided to the host by the antibodies, wherein the protective effect of the antibodies is synergistic.

6. The method of claim 1 wherein each antibody is administered as part of a separate composition.

7. The method of claim 1 wherein at least two of the antibodies are administered as part of a single composition.

8. The method of claim 1 wherein the antibodies are administered as part of a single composition.

9. The method of claim 1 wherein at least one of the antibodies is selected from the group consisting of a humanized antibody, chimeric antibody, F(ab')$_2$ fragment, Fab' fragment, Fab fragment, Fv fragment, and a single chain antibody.

10. The method of claim 1 wherein the at least two antibodies are selected from the group consisting of an F(ab')$_2$ fragment, single chain antibody, Fab' fragment, Fab fragment, and Fv fragment.

* * * * *